United States Patent [19]

Fujii, deceased et al.

[11] Patent Number: 5,240,845

[45] Date of Patent: Aug. 31, 1993

[54] MUTATED STREPTOKINASE PROTEINS

[75] Inventors: Setsuro Fujii, deceased, late of Kyoto, Japan, by Keiko Fujii, Shinichiro Fujii, heirs; Kaoruko Takada, heir, Ehime; Tamiki Katano, Itano; Eiji Majima; Koichi Ogino, both of Naruto; Kenji Ono; Yasuyo Sakata, both of Tokushima; Tsutomu Uenoyama, Naruto, all of Japan

[73] Assignee: Otsuka Pharmaceutical Factory, Ltd., Tokushima, Japan

[21] Appl. No.: 549,049

[22] Filed: Jul. 6, 1990

[30] Foreign Application Priority Data

Jul. 11, 1989 [JP] Japan .................................. 1-179432
Nov. 27, 1989 [JP] Japan .................................. 1-307957
Apr. 11, 1990 [JP] Japan .................................. 2-96830

[51] Int. Cl.$^5$ ...................... C12N 9/70; C12N 15/00; A61K 37/547
[52] U.S. Cl. ............................. 435/216; 435/172.3; 935/10; 935/14; 424/94.64
[58] Field of Search .............. 435/172.3, 216; 935/10, 935/14; 424/94.63, 94.64

[56] References Cited

FOREIGN PATENT DOCUMENTS 0407942 1/1991 European Pat. Off. .

OTHER PUBLICATIONS

Rajagopalan, et al., *J. Clin. Invest.*, vol. 75, Feb. 1985, pp. 413–419.
Jackson, et al., *Biochemistry*, vol. 25, No. 1, 1986, pp. 108–114.
Koide, et al., *FEBS Letters*, vol. 143, No. 1, Jun. 1982, pp. 73–76.
Jackson, et al., *Biochemistry*, vol. 21, No. 26, 1982, pp. 6620–6625.

*Primary Examiner*—Robert A. Wax
*Assistant Examiner*—Keith D. Hendricks
*Attorney, Agent, or Firm*—Armstrong, Westerman, Hattori, McLeland & Naughton

[57] ABSTRACT

This invention relates to a novel chemically synthesized gene including a base sequence coding for the primary amino acid sequence of natutal-type streptokinase, a corresponding plasmid recombinant, corresponding transformant and process for preparing streptokinase by the incubation of the transformant, the invention further relating to novel streptokinase derivative proteins having streptokinase activity and a modified primary amino acid sequence corresponding to the primary amino acid sequence of natural-type streptokinase which is deficient in the amino acid residues at the 373-position to the C-terminus, and wherein at least one of the amino acid residues may be deficient, replaced or inserted; the chemically synthesized gene including a base sequence coding for the derivative protein, plasmid containing the gene, transformant transformed by the plasmid, and process for preparing the streptokinase derivative protein by the incubation of the transformant.

14 Claims, 11 Drawing Sheets

MUTATED STREPTOKINASE PROTEINS

The present invention relates to a novel chemically synthesized gene including a base sequence coding for the primary amino acid sequence of streptokinase, a corresponding plasmid recombinant, corresponding transformant and process for preparing streptokinase by the incubation of the transformant, the invention further relating to novel streptokinase derivative proteins having a modified primary amino acid sequence, chemically synthesized gene including a base sequence coding for the protein, plasmid recombinant containing the gene, transformant transformed by the recombinant, and process for preparing the streptokinase derivative protein by the incubation of the transformant.

Streptokinase is a protein produced or secreted by hemolytic streptococci and having thrombolytic activity and a molecular weight of about 47000. The primary amino acid sequence of the protein is represented by the formula (1) given below. The total base sequence coding for the protein has also been determined from the DNA of *Streptococcus equisimilis* H46A (Group C) which produces the protein.

Streptokinase is already in clinical use as a thrombolytic agent in U.S. and European countries, is widely used for treating patients with lung thrombus and acute myocardial infarction and has been proved fully effective.

However, when streptokinase is prepared by incubating original bacteria, the resulting culture contains some extracellular secretions, many of which are toxic or likely to be toxic to humans, so that the preparation of streptokinase from the culture for clinical use requires many purification steps which must be executed with utmost care. Further it has been reported that the streptokinase obtained by the incubation of original bacteria cause various symptoms of shock due to the antigenicity thereof. It has therefore been desired in the art to develop techniques for reducing the antigenicity or to provide novel streptokinase derivatives with reduced antigenicity. For clinical use, it is also desired to improve streptokinase in its stability in blood and its specificity of thrombolytic activity.

An object of the present invention is to provide a process for preparing a large quantity of streptokinase with ease and high purity by resorting to gene recombination techniques, chemically synthesized gene of streptokinase wherein nucleotide codons are used to practice the process easily with use of *E. coli*, corresponding plasmid recombinant (streptokinase expression vector) having the gene introduced therein, host cell (transformant) transformed with the recombinant, and techniques for incubating the cell.

Another object of the invention is to provide a novel streptokinase derivative protein which has activities inherent in streptokinase, especially thrombolytic activity, and which is reduced in the binding activity to a streptokinase-specific antibody and in the productivity of the specific antibody (antigenicity) when the protein is administered.

Another object of the invention is to provide the derivative protein which is improved in its stability in blood and in thrombolytic specificity.

Another object of the invention is to provide a process for preparing the novel streptokinase derivative protein by utilizing gene recombination techniques capable of producing the protein in a large quantity with ease and high purify, chemically synthesized gene wherein nucleotide codons are used to practice the process easily with use of *E. coli*, corresponding plasmid recombinant (expression vector) having the gene inserted therein, host cell (transformant) transformed with the recombinant, and techniques for preparing the protein by incubating the cell.

The present invention provides a chemically synthesized gene coding for streptokinase of the natural-type having a primary amino acid sequence represented by the following formula (1), a corresponding plasmid recombinant having the gene introduced therein (natural-type streptokinase expression vector), a corresponding transformant obtained from the recombinant by transformation, and a process for preparing natural-type streptokinase by incubating the transformant.

Formula (1):
Ile—Ala—Gly—Pro—Glu—Trp—Leu—Leu—Asp—Arg—
Pro—Ser—Val—Asn—Asn—Ser—Gln—Leu—Val—Val—
Ser—Val—Ala—Gly—Thr—Val—Glu—Gly—Thr—Asn—
Gln—Asp—Ile—Ser—Leu—Lys—Phe—Phe—Glu—Ile—
Asp—Leu—Thr—Ser—Arg—Pro—Ala—His—Gly—Gly—
Lys—Thr—Glu—Gln—Gly—Leu—Ser—Pro—Lys—Ser—
Lys—Pro—Phe—Ala—Thr—Asp—Ser—Gly—Ala—Met—
Ser—His—Lys—Leu—Glu—Lys—Ala—Asp—Leu—Leu—
Lys—Ala—Ile—Gln—Glu—Gln—Leu—Ile—Ala—Asn—
Val—His—Ser—Asn—Asp—Asp—Tyr—Phe—Glu—Val—
Ile—Asp—Phe—Ala—Ser—Asp—Ala—Thr—Ile—Thr—
Asp—Arg—Asn—Gly—Lys—Val—Tyr—Phe—Ala—Asp—
Lys—Asp—Gly—Ser—Val—Thr—Leu—Pro—Thr—Gln—
Pro—Val—Gln—Glu—Phe—Leu—Leu—Ser—Gly—His—
Val—Arg—Val—Arg—Pro—Tyr—Lys—Glu—Lys—Pro—
Ile—Gln—Asn—Gln—Ala—Lys—Ser—Val—Asp—Val—
Glu—Tyr—Thr—Val—Gln—Phe—Thr—Pro—Leu—Asn—
Pro—Asp—Asp—Asp—Phe—Arg—Pro—Gly—Leu—Lys—
Asp—Thr—Lys—Leu—Leu—Lys—Thr—Leu—Ala—Ile—
Gly—Asp—Thr—Ile—Thr—Ser—Gln—Glu—Leu—Leu—
Ala—Gln—Ala—Gln—Ser—Ile—Leu—Asn—Lys—Asn—
His—Pro—Gly—Tyr—Thr—Ile—Tyr—Glu—Arg—Asp—
Ser—Ser—Ile—Val—Thr—His—Asp—Asn—Asp—Ile—
Phe—Arg—Thr—Ile—Leu—Pro—Met—Asp—Gln—Glu—
Phe—Thr—Tyr—Arg—Val—Lys—Asn—Arg—Glu—Gln—
Ala—Tyr—Arg—Ile—Asn—Lys—Lys—Ser—Gly—Leu—
Asn—Glu—Glu—Ile—Asn—Asn—Thr—Asp—Leu—Ile—
Ser—Glu—Lys—Tyr—Tyr—Val—Leu—Lys—Lys—Gly—
Glu—Lys—Pro—Tyr—Asp—Pro—Phe—Asp—Arg—Ser—
His—Leu—Lys—Leu—Phe—Thr—Ile—Lys—Tyr—Val—
Asp—Val—Asp—Thr—Asn—Glu—Leu—Leu—Lys—Ser—
Glu—Gln—Leu—Leu—Thr—Ala—Ser—Glu—Arg—Asn—
Leu—Asp—Phe—Arg—Asp—Leu—Tyr—Asp—Pro—Arg—
Asp—Lys—Ala—Lys—Leu—Leu—Tyr—Asn—Asn—Leu—
Asp—Ala—Phe—Gly—Ile—Met—Asp—Tyr—Thr—Leu—
Thr—Gly—Lys—Val—Glu—Asp—Asn—His—Asp—Asp—
Thr—Asn—Arg—Ile—Ile—Thr—Val—Tyr—Met—Gly—
Lys—Arg—Pro—Glu—Gly—Glu—Asn—Ala—Ser—Tyr—
His—Leu—Ala—Tyr—Asp—Lys—Asp—Arg—Tyr—Thr—
Glu—Glu—Glu—Arg—Glu—Val—Tyr—Ser—Tyr—Leu—
Arg—Tyr—Thr—Gly—Thr—Pro—Ile—Pro—Asp—Asn—
Pro—Asn—Asp—Lys The present invention further provides a streptokinase derivative protein which has a modified primary amino acid sequence corresponding to the amino acid sequence represented by the formula (1) of nature-type streptokinase which is deficient in the amino acid residues at the 373-position to the C-terminal and wherein at least one amino acid residue may optionally be deficient, replaced or inserted.

The symbols as used in the formula (1) and hereinafter to represent amino acid sequences and amino acid residues, as well as base sequences, nucleic acid bases, etc., are according to the nomenclature of IUPACIUB and to the practice in the art, as exemplified below.

| | |
|---|---|
| Ala: alanine | Arg: arginine |
| Asn: asparagine | Asp: aspartic acid |
| Cys: cysteine | Gln: glutamine |
| Glu: glutamic acid | Gly: glycine |
| His: histidine | Ile: isoleucine |
| Leu: leucine | Lys: lysine |
| Met: methioine | Phe: phenylalanine |
| Pro: proline | Ser: serine |
| Thr: threonine | Try: tryptophan |
| Tyr: tyrosine | Val: valine |
| A: adenine | T: thymine |
| G: guanine | C: cytosine |

The positions of the amino acid residues in amino acid sequences are all expressed according to the amino acid sequence of the formula (1) even when an amino acid or amino acids are deficient or inserted.

Given below are preferred examples of streptokinase derivative proteins of the invention having modified primary amino acid sequences.

(1) Polypeptide having the amino acid sequence (represented by the formula (1)) of natural-type streptokinase wherein the amino acid residues at the 373-position to the C-terminal are deficient.

(2) Polypeptide having the amino acid sequence of natural-type streptokinase wherein the amino acid residues at the 373-position to the C-terminal are deficient, and further the amino acid sequence of at least from Arg at the 45-position to Gly at the 68-position is deficient.

(3) Polypeptide having the amino acid sequence of natural-type streptokinase wherein the amino acid residues at the 373-position to the C-terminal are deficient, and further at least Phe at the 118-position is deficient or replaced by other amino acid residue.

(4) Polypeptide having the amino acid sequence of natural-type streptokinase wherein the amino acid residues at the 373-position to the C-terminal are deficient, and further at least Lys at the 256-position and Lys at the 257-position are deficient or replaced by other amino acid residues.

(5) Polypeptide having the amino acid sequence of natural-type streptokinase wherein the amino acid residues ar the 373-position to the C-terminal are deficient, and further other amino acid residue is inserted in the position next to at least each of Lys at the 256-position and Lys at the 257-position.

The other amino acid residue which can be substituted or inserted in the above modified amino acid sequences can be any of those constituting the protein of streptokinase and is preferably selected from among the α-amino acids constituting the proteins of the human body. Examples of such amino acids are Pro, Gln, Thr, Ser, His and the like. More specifically, examples of preferred amino acid residues to be substituted in the 256-position are Gln, Thr, His and the like. Those to be substituted in the 257-position are Pro, Gln, Ser and His. Those to be inserted in the 256- and 257-positions include Pro.

The present invention further provides a chemically synthesized gene including a base sequence coding for the streptokinase derivative protein having the modified amino acid sequence, a corresponding plasmid recombinant having the gene inserted therein (streptokinase derivative protein expression vector), a host cell transformed with the recombinant, and a process for preparing the streptokinase derivative protein by incubating the transformant.

A detail description will be given of the streptokinase derivative protein of the invention, the process for preparing the same and the process for preparing natural-type streptokinase of the invention as well as the chemically synthesized gene, the expression vector and the transformant which are used in these processes.

In accordance with the primary amino acid sequence of the formula (1), various base sequences can be determined for the chemically synthesized gene coding for the primary amino acid sequence of natural-type streptokinase of the invention. It is desirable to employ the following standards for this purpose.

1) Select triplet codons which are frequently used in the host cell, e.g., in *E. coli*.
2) Give specific restriction enzyme recognition sites within the base sequence to be determined and at the opposite ends thereof to ensure facilitated ligation to the base sequence of other gene or the like and facilitated insertion into the plasmid vector utilizing these sites as desired.
3) In joining or ligating chemically synthesized genes (DNA fragments), avoid or minimize ligations other than the desired ligation.
4) Eliminate objectionable sequences, such as terminator, from the base sequence to be designed.
5) Provide a restriction enzyme recognition site ar a suitable position so as to facilitate the subsequent modification of the gene.

The formula (2) given below represents a preferred example of base sequence thus determined of chemically synthesized gene of natural-type streptokinase. The corresponding amino acid sequence is also given.

Formula (2):
5' ATC GCG GGC CCG GAA TGG CTG CTG GAC CGT
3' TAG CGC CCG GGC CTT ACC GAC GAC CTG GCA
Ile— Ala—Gly—Pro—Glu—Trp—Leu—Leu—Asp—Arg—

CCG TCT GTT AAC AAC TCC CAG CTG GTT GTT
GGC AGA CAA TTG TTG AGG GTC GAC CAA CAA
Pro—Ser— Val—Asn—Asn—Ser— Gln—Leu—Val—Val—

TCC GTA GCT GGC ACT GTT GAA GGT ACT AAC
AGG CAT CGA CCG TGA CAA CTT CCA TGA TTG
Ser— Val—Ala—Gly—Thr—Val—Glu—Gly—Thr—Asn—

CAG GAC ATC TCT CTG AAA TTT TTC GAA ATC
GTC CTG TAG AGA GAC TTT AAA AAG CTT TAG
Gln—Asp—Ile— Ser—Leu—Lys—Phe—Phe—Glu—Ile—

GAC CTG ACC TCT CGT CCG GCC CAT GGT GGT
CTG GAC TGG AGA GCA GGC CGG GTA CCA CCA
Asp—Leu—Thr—Ser—Arg—Pro—Ala—His—Gly—Gly—

AAA ACC GAA CAG GGC CTG TCC CCG AAA TCT
TTT TGG CTT GTC CCG GAC AGG GGC TTT AGA
Lys—Thr—Glu—Gln—Gly—Leu—Ser— Pro—Lys—Ser—

AAA CCG TTC GCT ACT GAC TCT GGC GCT ATG
TTT GGC AAG CGA TGA CTG AGA CCG CGA TAC
Lys—Pro—Phe—Ala—Thr—Asp—Ser—Gly—Ala—Met—

TCT CAT AAA CTC GAG AAG GCA GAT CTG CTG
AGA GTA TTT GAG CTC TTC CGT CTA GAC GAC
Ser— His—Lys—Leu—Glu—Lys—Ala—Asp—Leu—Leu—

AAA GCA ATC CAG GAA CAG CTG ATC GCT AAC
TTT CGT TAG GTC CTT GTC GAC TAG CGA TTG
Lys—Ala—Ile— Gln—Glu—Gln—Leu—Ile— Ala—Asn—

GTA CAT TCT AAC GAC GAC TAC TTT GAG GTA
CAT GTA AGA TTG CTG CTG ATG AAA CTC CAT
Val—His—Ser— Asn—Asp—Asp—Tyr—Phe—Glu—Val—

-continued
```
ATC GAC TTC GCT AGC GAC GCT ACT ATC ACC
TAG CTG AAG CGA TCG CTG CGA TGA TAG TGG
Ile— Asp—Phe—Ala—Ser—Asp—Ala—Thr—Ile— Thr—

GAC CGT AAC GGC AAA GTA TAC TTC GCT GAC
CTG GCA TTG CCG TTT CAT ATG AAG CGA CTG
Asp—Arg—Asn—Gly—Lys—Val—Tyr—Phe—Ala—Asp—

AAA GAC GGT TCT GTA ACT CTT CCG ACT CAA
TTT CTG CCA AGA CAT TGA GAA GGC TGA GTT
Lys—Asp—Gly—Ser— Val—Thr—Leu—Pro—Thr—Gln—

CCG GTA CAG GAA TTT CTG CTG TCT GGC CAT
GGC CAT GTC CTT AAA GAC GAC AGA CCG GTA
Pro—Val—Gln—Glu—Phe—Leu—Leu—Ser— Gly—His—

GTA CGC GTT CGC CCG TAC AAA GAA AAA CCG
CAT GCG CAA GCG GGC ATG TTT CTT TTT GGC
Val—Arg—Val—Arg—Pro—Tyr—Lys—Glu—Lys—Pro—

ATC CAG AAC CAG GCT AAA TCT GTT GAC GTA
TAG GTC TTG GTC CGA TTT AGA CAA CTG CAT
Ile— Gln—Asn—Gln—Ala—Lys—Ser— Val—Asp—Val—

GAA TAC ACC GTT CAG TTC ACC CCG CTG AAC
CTT ATG TGG CAA GTC AAG TGG GGC GAC TTG
Glu—Tyr—Thr—Val—Gln—Phe—Thr—Pro—Leu—Asn—

CCA GAC GAT GAC TTC CGC CCG GGT CTG AAA
GGT CTG CTA CTG AAG GCG GGC CCA GAC TTT
Pro—Asp—Asp—Asp—Phe—Arg—Pro—Gly—Leu—Lys—

GAC ACT AAA CTG CTG AAA ACC CTG GCT ATC
CTG TGA TTT GAC GAC TTT TGG GAC CGA TAG
Asp—Thr—Lys—Leu—Leu—Lys—Thr—Leu—Ala—Ile—

GGT GAC ACC ATC ACT TCT CAG GAG CTC CTG
CCA CTG TGG TAG TGA AGA GTC CTC GAG GAC
Gly—Asp—Thr—Ile— Thr—Ser— Gln—Glu—Leu—Leu—

GCT CAG GCA CAG TCT ATC CTG AAC AAA AAC
CGA GTC CGT GTC AGA TAG GAC TTG TTT TTG
Ala—Gln—Ala—Gln—Ser— Ile— Leu—Asn—Lys—Asn—

CAT CCG GGC TAC ACT ATC TAC GAA CGC GAC
GTA GGC CCG ATG TGA TAG ATG CTT GCG CTG
His—Pro—Gly—Tyr—Thr—Ile— Tyr—Glu—Arg—Asp—

TCT TCC ATC GTA ACC CAT GAC AAC GAC ATC
AGA AGG TAG CAT TGG GTA CTG TTG CTG TAG
Ser— Ser— Ile— Val—Thr—His—Asp—Asn—Asp—Ile—

TTC CGT ACC ATT CTG CCG ATG GAC CAG GAA
AAG GCA TGG TAA GAC GGC TAC CTG GTC CTT
Phe—Arg—Thr—Ile— Leu—Pro—Met—Asp—Gln—Glu—

TTT ACT TAC CGT GTT AAA AAC CGC GAA CAA
AAA TGA ATG GCA CAA TTT TTG GCG CTT GTT
Phe—Thr—Tyr—Arg—Val—Lys—Asn—Arg—Glu—Gln—

GCT TAC CGT ATC AAT AAA AAA TCC GGT CTG
CGA ATG GCA TAG TTA TTT TTT AGG CCA GAC
Ala—Tyr—Arg—Ile— Asn—Lys—Lys—Ser— Gly—Leu—

AAT GAA GAG ATT AAC AAC ACT GAC CTG ATC
TTA CTT CTC TAA TTG TTG TGA CTG GAC TAG
Asn—Glu—Glu—Ile— Asn—Asn—Thr—Asp—Leu—Ile—

TCT GAA AAG TAC TAC GTA CTG AAA AAA GGT
AGA CTT TTC ATG ATG CAT GAC TTT TTT CCA
Ser— Glu—Lys—Tyr—Tyr—Val—Leu—Lys—Lys—Gly—

GAG AAG CCG TAT GAC CCG TTC GAT CGT TCT
CTC TTC GGC ATA CTG GGC AAG CTA GCA AGA
Glu—Lys—Pro—Tyr—Asp—Pro—Phe—Asp—Arg—Ser—

CAT CTG AAA CTG TTC ACC ATC AAA TAC GTT
GTA GAC TTT GAC AAG TGG TAG TTT ATG CAA
His—Leu—Lys—Leu—Phe—Thr—Ile— Lys—Tyr—Val—

GAC GTC GAT ACC AAC GAA TTA CTG AAG TCT
CTG CAG CTA TGG TTG CTT AAT GAC TTC AGA
Asp—Val—Asp—Thr—Asn—Glu—Leu—Leu—Lys—Ser—

GAG CAG CTG CTG ACC GCT TCC GAA CGT AAT
CTC GTC GAC GAC TGG CGA AGG CTT GCA TTA
Glu—Gln—Leu—Leu—Thr—Ala—Ser— Glu—Arg—Asn—

CTG GAC TTC CGC GAT CTG TAC GAC CCG CGT
GAC CTG AAG GCG CTA GAC ATG CTG GGC GCA
Leu—Asp—Phe—Arg—Asp—Leu—Tyr—Asp—Pro—Arg—

GAC AAA GCT AAA CTG CTG TAC AAC AAC CTG
CTG TTT CGA TTT GAC GAC ATG TTG TTG GAC
Asp—Lys—Ala—Lys—Leu—Leu—Tyr—Asn—Asn—Leu—

GAT GCT TTC GGT ATC ATG GAC TAC ACC CTG
CTA CGA AAG CCA TAG TAC CTG ATG TGG GAC
Asp—Ala—Phe—Gly—Ile— Met—Asp—Tyr—Thr—Leu—

ACT GGT AAA GTA GAA GAC AAC CAT GAC GAC
TGA CCA TTT CAT CTT CTG TTG GTA CTG CTG
Thr—Gly—Lys—Val—Glu—Asp—Asn—His—Asp—Asp—

ACC AAC CGT ATC ATC ACC GTA TAC ATG GGC
TGG TTG GCA TAG TAG TGG CAT ATG TAC CCG
Thr—Asn—Arg—Ile— Ile— Thr—Val—Tyr—Met—Gly—

AAA CGT CCG GAA GGT GAA AAT GCA TCT TAC
TTT GCA GGC CTT CCA CTT TTA CGT AGA ATG
Lys—Arg—Pro—Glu—Gly—Glu—Asn—Ala—Ser— Tyr—

CAT CTG GCA TAT GAC AAA GAC CGT TAC ACC
GTA GAC CGT ATA CTG TTT CTG GCA ATG TGG
His—Leu—Ala—Tyr—Asp—Lys—Asp—Arg—Tyr—Thr—

GAA GAA GAA CGT GAA GTT TAC TCT TAC CTG
CTT CTT CTT GCA CTT CAA ATG AGA ATG GAC
Glu—Glu—Glu—Arg—Glu—Val—Tyr—Ser— Tyr—Leu—

CGC TAT ACT GGT ACC CCT ATC CCG GAT AAC
GCG ATA TGA CCA TGG GGA TAG GGC CTA TTG
Arg—Tyr—Thr—Gly—Thr—Pro—Ile— Pro—Asp—Asn—

CCG AAC GAT AAA 3'
GGC TTG CTA TTT 5'
Pro—Asn—Asp—Lys
```

The base sequence represented by the formula (2) is in the form of a double-stranded DNA sequence coding for the primary amino acid sequence (formula (1)) of natural-type streptokinase and comprising single-stranded DNA sequences which are complementary to each other. These complementary DNA sequences are also included in the present invention.

In view of the use of E. coli as the host cell, codons which are frequently used for E. coli are preferentially selected for designing the base sequence of the formula (2), whereas the codons to be used for the present gene are not limited to such codons. Furthermore, the host cells to be used in the present invention are not limited to those of E. coli as will be described later. Accordingly, codons which are frequently used in the host cell can be selected for use in combination. More specifically, the base sequence of the desired gene can be the base sequence of any chemically synthesized gene insofar as the sequence has the same generic information as the base sequence of the formula (2), i.e., insofar as the base sequence contains the one coding for the primary amino acid sequence of streptokinase so that streptokinase can be expressed and produced by gene recombination techniques. Thus, the base sequence of the formula (2) can be altered or modified by local change, deletion or addition of some nucleic acid bases. Such alteration or modification of the base sequence includes use of genetic codons coding for the same primary amino acid sequence as the one coded for by the base sequence of the formula (2), and provision of various restriction enzyme recognition sites for effecting ligation with regulators, such as promoter, which are required in actually inserting the resulting base sequence into a suitable vector for expression in a microorganism. In constructing the desired expression vector by gene engineering techniques utilizing the gene of the present invention, it is necessary to suitably attach various regulators such as promoter, Shine-Dalgarno sequence (SD sequence) and like ribosomal binding sites, protein synthesis initiation codon and termination codon, etc. Since the ligation and cleavage of base sequences are effected with use of restriction enzymes, there is a need to provide suitable restriction enzyme recognition site at the upstream and downstream ends thereof. The formula (3) given below represents an example of gene wherein such suitable restriction enzyme recognition sites are attached. The gene comprises the base sequence of the formula (2) and specific restriction enzyme recognition sites provided at the upstream and downstream ends thereof for attaching promoter and like regulators which are required for the expression of the desired protein encoded by the base sequence. The gene is desirable for the subsequent construction of expression vector. The restriction enzyme recognition sites present in the base sequence of the formula (3) are shown by the formula (4). Of course, the formula (4) shows only examples of recognition sites; those to be present in the gene of the invention can be suitably modified or selected in accordance with the kind of expression vector to be constructed.

Formula (3):

| | | | | 5' AA | TTC | GGA | TCC | ATG |
|---|---|---|---|---|---|---|---|---|
| | | | | 3'  G | CCT | AGG | TAC |   |
| ATC | GCG | GGC | CCG | GAA | TGG | CTG | CTG | GAC | CGT |
| TAG | CGC | CCG | GGC | CTT | ACC | GAC | GAC | CTG | GCA |
| CCG | TCT | GTT | AAC | AAC | TCC | CAG | CTG | GTT | GTT |
| GGC | AGA | CAA | TTG | TTG | AGG | GTC | GAC | CAA | CAA |
| TCC | GTA | GCT | GGC | ACT | GTT | GAA | GGT | ACT | AAC |
| AGG | CAT | CGA | CCG | TGA | CAA | CTT | CCA | TGA | TTG |
| CAG | GAC | ATC | TCT | CTG | AAA | TTT | TTC | GAA | ATC |
| GTC | CTG | TAG | AGA | GAC | TTT | AAA | AAG | CTT | TAG |
| GAC | CTG | ACC | TCT | CGT | CCG | GCC | CAT | GGT | GGT |
| CTG | GAC | TGG | AGA | GCA | GGC | CGG | GTA | CCA | CCA |
| AAA | ACC | GAA | CAG | GGC | CTG | TCC | CCG | AAA | TCT |
| TTT | TGG | CTT | GTC | CCG | GAC | AGG | GGC | TTT | AGA |
| AAA | CCG | TTC | GCT | ACT | GAC | TCT | GGC | GCT | ATG |
| TTT | GGC | AAG | CGA | TGA | CTG | AGA | CCG | CGA | TAC |
| TCT | CAT | AAA | CTC | GAG | AAG | GCA | GAT | CTG | CTG |
| AGA | GTA | TTT | GAG | CTC | TTC | CGT | CTA | GAC | GAC |
| AAA | GCA | ATC | CAG | GAA | CAG | CTG | ATC | GCT | AAC |
| TTT | CGT | TAG | GTC | CTT | GTC | GAC | TAG | CGA | TTG |
| GTA | CAT | TCT | AAC | GAC | GAC | TAC | TTT | GAG | GTA |
| CAT | GTA | AGA | TTG | CTG | CTG | ATG | AAA | CTC | CAT |
| ATC | GAC | TTC | GCT | AGC | GAC | GCT | ACT | ATC | ACC |
| TAG | CTG | AAG | CGA | TCG | CTG | CGA | TGA | TAG | TGG |
| GAC | CGT | AAC | GGC | AAA | GTA | TAC | TTC | GCT | GAC |
| CTG | GCA | TTG | CCG | TTT | CAT | ATG | AAG | CGA | CTG |
| AAA | GAC | GGT | TCT | GTA | ACT | CTT | CCG | ACT | CAA |
| TTT | CTG | CCA | AGA | CAT | TGA | GAA | GGC | TGA | GTT |
| CCG | GTA | CAG | GAA | TTT | CTG | CTG | TCT | GGC | CAT |
| GGC | CAT | GTC | CTT | AAA | GAC | GAC | AGA | CCG | GTA |
| GTA | CGC | GTT | CGC | CCG | TAC | AAA | GAA | AAA | CCG |
| CAT | GCG | CAA | GCG | GGC | ATG | TTT | CTT | TTT | GGC |
| ATC | CAG | AAC | CAG | GCT | AAA | TCT | GTT | GAC | GTA |
| TAG | GTC | TTG | GTC | CGA | TTT | AGA | CAA | CTG | CAT |
| GAA | TAC | ACC | GTT | CAG | TTC | ACC | CCG | CTG | AAC |
| CTT | ATG | TGG | CAA | GTC | AAG | TGG | GGC | GAC | TTG |
| CCA | GAC | GAT | GAC | TTC | CGC | CCG | GGT | CTG | AAA |
| GGT | CTG | CTA | CTG | AAG | GCG | GGC | CCA | GAC | TTT |
| GAC | ACT | AAA | CTG | CTG | AAA | ACC | CTG | GCT | ATC |
| CTG | TGA | TTT | GAC | GAC | TTT | TGG | GAC | CGA | TAG |
| GGT | GAC | ACC | ATC | ACT | TCT | CAG | GAG | CTC | CTG |
| CCA | CTG | TGG | TAG | TGA | AGA | GTC | CTC | GAG | GAC |

-continued

```
GCT  CAG  GCA  CAG  TCT  ATC  CTG  AAC  AAA  AAC
CGA  GTC  CGT  GTC  AGA  TAG  GAC  TTG  TTT  TTG

CAT  CCG  GGC  TAC  ACT  ATC  TAC  GAA  CGC  GAC
GTA  GGC  CCG  ATG  TGA  TAG  ATG  CTT  GCG  CTG

TCT  TCC  ATC  GTA  ACC  CAT  GAC  AAC  GAC  ATC
AGA  AGG  TAG  CAT  TGG  GTA  CTG  TTG  CTG  TAG

TTC  CGT  ACC  ATT  CTG  CCG  ATG  GAC  CAG  GAA
AAG  GCA  TGG  TAA  GAC  GGC  TAC  CTG  GTC  CTT

TTT  ACT  TAC  CGT  GTT  AAA  AAC  CGC  GAA  CAA
AAA  TGA  ATG  GCA  CAA  TTT  TTG  GCG  CTT  GTT

GCT  TAC  CGT  ATC  AAT  AAA  AAA  TCC  GGT  CTG
CGA  ATG  GCA  TAG  TTA  TTT  TTT  AGG  CCA  GAC

AAT  GAA  GAG  ATT  AAC  AAC  ACT  GAC  CTG  ATC
TTA  CTT  CTC  TAA  TTG  TTG  TGA  CTG  GAC  TAG

TCT  GAA  AAG  TAC  TAC  GTA  CTG  AAA  AAA  GGT
AGA  CTT  TTC  ATG  ATG  CAT  GAC  TTT  TTT  CCA

GAG  AAG  CCG  TAT  GAC  CCG  TTC  GAT  CGT  TCT
CTC  TTC  GGC  ATA  CTG  GGC  AAG  CTA  GCA  AGA

CAT  CTG  AAA  CTG  TTC  ACC  ATC  AAA  TAC  GTT
GTA  GAC  TTT  GAC  AAG  TGG  TAG  TTT  ATG  CAA

GAC  GTC  GAT  ACC  AAC  GAA  TTA  CTG  AAG  TCT
CTG  CAG  CTA  TGG  TTG  CTT  AAT  GAC  TTC  AGA

GAG  CAG  CTG  CTG  ACC  GCT  TCC  GAA  CGT  AAT
CTC  GTC  GAC  GAC  TGG  CGA  AGG  CTT  GCA  TTA

CTG  GAC  TTC  CGC  GAT  CTG  TAC  GAC  CCG  CGT
GAC  CTG  AAG  GCG  CTA  GAC  ATG  CTG  GGC  GCA

GAC  AAA  GCT  AAA  CTG  CTG  TAC  AAC  AAC  CTG
CTG  TTT  CGA  TTT  GAC  GAC  ATG  TTG  TTG  GAC

GAT  GCT  TTC  GGT  ATC  ATG  GAC  TAC  ACC  CTG
CTA  CGA  AAG  CCA  TAG  TAC  CTG  ATG  TGG  GAC

ACT  GGT  AAA  GTA  GAA  GAC  AAC  CAT  GAC  GAC
TGA  CCA  TTT  CAT  CTT  CTG  TTG  GTA  CTG  CTG

ACC  AAC  CGT  ATC  ATC  ACC  GTA  TAC  ATG  GGC
TGG  TTG  GCA  TAG  TAG  TGG  CAT  ATG  TAC  CCG

AAA  CGT  CCG  GAA  GGT  GAA  AAT  GCA  TCT  TAC
TTT  GCA  GGC  CTT  CCA  CTT  TTA  CGT  AGA  ATG

CAT  CTG  GCA  TAT  GAC  AAA  GAC  CGT  TAC  ACC
GTA  GAC  CGT  ATA  CTG  TTT  CTG  GCA  ATG  TGG

GAA  GAA  GAA  CGT  GAA  GTT  TAC  TCT  TAC  CTG
CTT  CTT  CTT  GCA  CTT  CAA  ATG  AGA  ATG  GAC

CGC  TAT  ACT  GGT  ACC  CCT  ATC  CCG  GAT  AAC
GCG  ATA  TGA  CCA  TGG  GGA  TAG  GGC  CTA  TTG

CCG  AAC  GAT  AAA  TAA  TAG           3'
GGC  TTG  CTA  TTT  ATT  ATC  AGCT      5'
```

Formula (4):

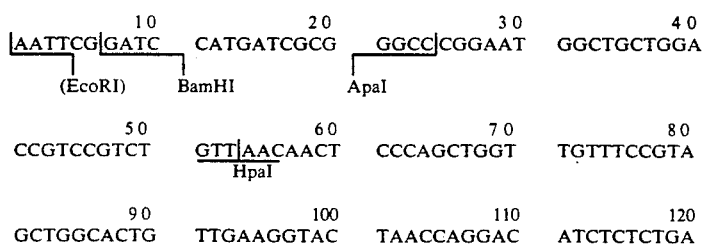

-continued

```
        130         140         150         160
   AATTTTTCGA  AATCGACCTG  ACCTCTCGTC  CGGCC|CATGG
                                              |
                                           NcoI, StyI 170         180         190         200
   TGGTAAAACC  GAACAGGGCC  TGTCCCCGAA  ATCTAAACCG 210         220         230         240
   TTCGCTACTG  ACTCTGGCGC  TATGTCTCAT  AAAC|TCGAGA
                        |
                      HaeII                AvaI, XhoI 250         260         270         280
   AGGCA|GATCT  GCTGAAAGCA  ATCCAGGAAC  AGCTGATCGC
            |
          BglII 290         300         310         320
   TAACGTACAT  TCTAACGACG  ACTACTTTGA  GGTAATCGAC 330         340         350         360
   TTCG|CTAGCG  ACGCTACTAT  CACCGACCGT  AACGGCAAAG
           |
         NheI 370         380         390         400
   T|ATACTTCGC  TGACAAAGAC  GGTTCTGTAA  CTCTTCCGAC
    |
   AccI 410         420         430         440
   TCAACCGGTA  CAGGAATTTC  TGCTGTCTGG  CCATGTA|CGC
                                      |
                                    BalI 450         460         470         480
   GTTCGCCCGT  ACAAAGAAAA  ACCGATCCAG  AACCAGGCTA
   |
   MluI 490         500         510         520
   AATCTGTTGA  CGTAGAATAC  ACCGTTCAGT  TCACCCCGCT 530         540         550         560
   GAACCCAGAC  GATGACTTCC  GC|CCGGGTCT  GAAAGACACT
                             |
                          SmaI,   └─AvaI, XmaI 570         580         590         600
   AAACTGCTGA  AAACCCTGGC  TATCGGTGAC  ACCATCACTT 610         620         630         640
   CTCAGGAGCT  CCTGGCTCAG  GCACAGTCTA  TCCTGAACAA
             |
          SacI, SstI 650         660         670         680
   AAACCATCCG  GGCTACACTA  TCTACGAACG  CGACTCTTCC 690         700         710         720
   ATCGTAACCC  ATGACAACGA  CATCTTCCGT  ACCATTCTGC 730         740         750         760
   CGATGGACCA  GGAATTTACT  TACCGTGTTA  AAAACCGCGA 770         780         790         800
   ACA|AGCTTAC  CGTATCAATA  AAAAATCCGG  TCTGAATGAA
         |
       HindIII 810         820         830         840
   GAGATTAACA  ACACTGACCT  GATCTCTGAA  AAGTACTACG
                                              | |
                                           ScaI SnaBI
```

-continued

```
       850           860           870           880
  TACTGAAAAA    AGGTGAGAAG    CCGTATGACC    CGTTCGAT|CG
                                                    |
                                                   PvuI 890           900           910           920
  TTCTCATCTG    AAACTGTTCA    CCATCAAATA    CGTTGA CGT|C
                                                    |
                                                   AatII 930           940           950           960
  GATACCAACG    AATTACTGAA    GTCTGAGCAG    CTGCTGACCG 970           980           990          1000
  CTTCCGAACG    TAATCTGGAC    TTCCGCGATC    TGTACGACCC 1010          1020          1030          1040
  GCGTGACAAA    GCTAAACTGC    TGTACAACAA    CCTGGATGCT 1050          1060          1070          1080
  TTCGGTATCA    TGGACTACAC    CCTGACTGGT    AAAGTAGAAG 1090          1100          1110          1120
  ACAACCATGA    CGACACCAAC    CGTATCATCA    CCGT|ATACAT
                                                |
                                               AccI 1130          1140          1150          1160
  GGGCAAACGT    CCGGAAGGTG    AAAATGCA|TC    TTACCATCTG
                                       |
                                      NsiI 1170          1180          1190          1200
  GCA|TATGACA   AAGACCGTTA    CACCGAAGAA    GAACGTGAAG
     |
    NdeI 1210          1220          1230          1240
  TTTACTCTTA    CCTGCGCTAT    ACTGGTAC|CC   CTATCCCGGA
                                       |
                                      KpnI 1250          1260
  TAACCCGAAC    GATAAATAAT    AG|
                                |
                              (SalI)
```

The chemically synthesized gene coding for the streptokinase derivative protein of the invention having a modified primary amino acid sequence can be designed based on the gene coding for natural-type streptokinase, using a DNA sequence (codons) coding for amino acid residues corresponding to the modification of the primary amino acid sequence. A specific portion of the DNA sequence can be modified by various methods known in the art. The modification procedure includes cleavage or removal of a specified region with use of restriction enzymes, or replacement of a specific region by a chemically synthesized oligonucleotide including a modified portion which is separately prepared.

Preferably, the chemically synthesized gene of the present invention is prepared by chemically synthesizing some oligonucleotide fragments according to the base sequence designed and ligating these fragments. The oligonucleotide fragments can be chemically synthesized with ease by usual methods using a commercial DNA synthesizer or the like. These methods include, for example, the solid-phase phosphite triester method [Nature, 310, 105(1984)] and the solid-phase phosphoamidide method (S. L. Beaucage and M. H. Carutheys, Tetrahedron Letters, 22, 1859(1981)). The oligonucleotide fragments prepared can be isolated and purified by a usual method such as high performance liquid chromatography. The purified base sequences can be checked, for example, by the Maxam-Gilbert method [A. M. Maxam and W. Gilbert, Proc. Natl. Acad. Sci., U.S.A., 74, 560 (1977); A. M. Maxam and W. Gilbert, Methods in Enzymol., 65, 499, Acad. Press (1980)].

The desired gene of the invention can be constructed by phosphorylating the resulting oligonucleotides at the hydroxyl groups of their 5' ends with T4 polynucleotidekinase, followed by annealing, ligating the oligonucleotides into blocks with use of T4 DNA ligase, similarly ligating the blocks into some subunits, and ligating the subunits. These subunits and the desired gene can be incorporated into suitable vectors, e.g. pBR322, for preservation or amplification. It is desirable to isolate the subunits or the gene from the vector for use in the subsequent procedure. The above gene preparation procedure is described specifically in examples given later.

The plasmid vector can be constructed by employing usual procedures or methods of gene engineering techniques. These include cleavage of DNA with restriction enzymes, S1 nuclease and the like, ligation of DNA fragments with T4 DNA ligase or the like, isolation and purification of DNA by agarose gel electrophoresis, polyacrylamide gel electrophoresis or the like, collection and purification of DNA by the phenol extraction method, etc. The host cells can be checked for the presence of the plasmid vector by the alkali SDS extraction method [H. C. Birnboim and J. Doly, Nucleic Acids Res., 7, 1513 (1979)], i.e., by treating the plasmid DNA collected therefrom with restriction enzymes and checking the DNA for the presence of corresponding restriction enzyme recognition sites or checking the length of DNA fragment produced. The presence of the vector can be checked also by analyzing the base sequence of the gene by the direct dideoxy method [F. Sanger et al., Proc., Natl. Acad. Sci., U.S.A., 74, 5463 (1977)] or like method.

Suitable vectors for use in constructing the plasmid recombinant incorporating the gene of the invention are pBR322 and various plasmid vectors derived therefrom. However, useful vectors are not limited to these but include various known ones such as bacteriophage, virus vectors inclusive of animal and vegetable viruses, plasmids, cosmids and the like.

For the transformant obtained by incorporating the vector to express the desired streptokinase or the protein of a derivative thereof, the vector needs to have, in addition to the gene of the invention, various regulators such as promoter, terminator, poly-A tail adding signal (in the case where the host cells are eucaryotic cells) and the like for transcription, and ribosomal binding site and the like for translation. Various promoters are known in different host cells. Examples of promoters in $E.$ $coli$ are trp promoter, lac promoter, tac promoter, $\lambda P_L$ promoter, lpp promoter and the like, those in Bacillus subtilis are SP01 promoter, SP02 promoter, pen promoter and the like, those in yeast and other eucaryotic cells are PH05 promoter, PGK promoter, SV40-derived promoter and the like. The desired vector of the invention can be obtained by selecting a plasmid containing such regulators as a vector, or isolating such regulators from a plasmid by the usual method or chemically synthesizing the regulators and incorporating the regulators into a suitable vector.

The vector (recombinant) obtained for expressing streptokinase or derivative protein thereof has the gene of the invention, promoter and ribosomal binding site which are bound to the upstream of the gene, and a terminator binding to the downstream thereof, i.e., information for expressing streptokinase (natural type or derivative) protein. The vector is introduced into suitable host cells, whereby the cells were caused to express (produce or accumulate) the protein of contemplated streptokinase or a derivative thereof.

Especially in the case where $E.$ $coli$ is used as the host cell, the expression vector includes a system for directly expressing the desired protein in the cell, and a system for causing the periplasm to secrete the protein for expression. In the secreting expression system, it is necessary to construct a vector having the chemically synthesized gene of the invention and a gene coding for a signal peptide bound to the upstream end of the gene. The secreting expression vector will be described below in detail.

The term "signal peptide" refers an amino acid sequence of more than ten to several tens of hydrophobic amino acid residues which is present at the amino ends of various secretory proteins. The signal peptide acts to withdraw the protein from the cytoplasm and is excised from the secretory protein by signal peptidase. The use of such signal peptides in gene recombination methods and the resulting advantages are known as described in detail, for example, in Unexamined Japanese Patent Publication SHO 61-149089.

The signal peptide to be used in the present invention may be the same as, or different from, those disclosed in the publication. Examples of useful signal peptides are $E.$ $coli$ $\beta$-lactamase (bla), alkaline phosphatase (pho S), $E.$ $coli$ outer membrane protein (Omp A, Omp F, Lpp) and the like.

The base sequence coding for such a signal peptide can be chemically synthesized, or a natural one can be utilized. pKTN mentioned in examples given later is an example of vector containing such a base sequence.

pKTN is a vector containing a base sequence coding for $E.$ $coli$ bla signal peptide, more specifically, a vector having gene information comprising tac promoter, SD sequence, and base sequence coding for bla signal peptide, as arranged in the same direction. $E.$ $coli$, the strain JM103 harboring pKTN has been deposited with the designation "*Escherichia coli*, JM-103, pKTN-2-2" and the deposition number FERM P-9146.

A preferred example of secreting expression system is the plasmid pSKXT constructed with use of pKTN as will be described later in an example. The secreting expression vector pSKXT has a base sequence which comprises the bla signal peptide encoded base sequence and a first codon coding for the amino acid residue at the first position of the streptokinase and directly attached to the downstream end of the base sequence, i.e., a base sequence coding for the fusion protein of the signal peptide and streptokinase. With this vector there is no likelihood of displacement of the reading frame, permitting $E.$ $coli$ cell to express the fusion protein by virtue of the action of tac promoter, such that the desired protein only is passed through the inner membrane and secreted and accumulated in the periplasm.

$E.$ $coli$, the strain JM109 harboring the plasmid pSKXT has been deposited in Fermentation Research Institute, Agency of Industrial Science and Technology, MITI with the designation "*Escherichia coli*, JM-109, pSKT" and the deposition number FERM BP-2464.

The desired expression vector thus obtained is introduced into suitable host cells (transformation), whereby the cells are given ability to produce streptokinase or protein of derivative thereof. The host cell to be used is not limited specifically but can be any of those known, such as cells of $E.$ $coli$ and like gram-negative bacteria, *Bacillus subtilis* and like gram-positive bacteria, actinomycetes and yeast, and animal or vegetable cells. Among these, $E.$ $coli$ is preferable, which are more preferably the strain HB101 [H. W. Boyer and D. Roulland-Dussoix., J. Mol. Biol., 41, 459 (1969)] and the strain JM109 [J. Messing et al., Nucleic Acids Res., 9, 309 (1981)] derived from the strain K12.

The vector of the invention can be introduced into the host cell for transformation by a usual method, for example, by treating the host cell in an aqueous solution containing calcium chloride at a low temperature and adding the vector to the solution [E. Lederberg and S. Cohen, J. Bacteriol., 119, 1072 (1974)].

The present invention also provides the host cell thus transformed (transformant having introduced therein the vector for expressing natural-type streptokinase of the invention or streptokinase derivative protein of the invention).

The transformant can be incubated using usual media, which include, for example, L-broth medium, E medium, M-g medium, etc. These media are usable with addition of various carbon sources, nitrogen sources, inorganic salts, vitamins, natural extracts, physiologically active substances and the like which are generally known.

The incubation can be carried out by various methods under conditions which are suitable to the growth of the host cell in respect of pH, temperature, aeration, stirring, etc. For example, it is desirable to incubate *E. coli* at a pH of about 5 to about 8, more preferably 7, at a temperature of about 20° to about 43° C. with aeration and stirring. The scale of incubation is not limited specifically. The composition of the medium and incubation conditions can be altered suitably in order to produce an increased amount of expressed protein or promote or inhibit the secretion of the desired protein.

For example, when *E. coli* is thus incubated which is transformed with a vector for secreting and expressing the streptokinase of the invention or protein of a derivative thereof, the desired protein is secreted and accumulated in the periplasm, and the protein can be separated off, collected and purified by usual methods. For this purpose, for example, the periplasm prepared by the osmotic shock method can be subjected to gel filtration, adsorption chromatography, ion-exchange chromatography, high performance liquid chromatography or the like method. Such methods can be employed in a suitable combination. The protein secreted in the periplasm or obtained in the culture supernatant is advantageous in that it is easy to separate off and purify by the above procedure.

In this way, streptokinase and protein of derivative thereof can be prepared by gene engineering techniques according to the present invention. The protein obtained can be readily identified with reference to the fact that it exhibits a single peak when subjected to high performance liquid chromatography or a single band when subjected to polyacrylamide gel electrophoresis. The desired streptokinase or derivative protein thereof, as purified to a higher degree, can be identified by the same methods as usually used for analyzing the structure of polypeptides or proteins, for example, by analyzing the molecular weight by SDS-PAGE, measuring isoelectric point by isoelectric focusing, determining the amino acid composition by amino acid analyzer, analyzing the amino acid sequence by protein sequencer, etc.

More advantageously, the streptokinase derivative protein having a modified primary amino acid sequence of the invention can be produced by preparing a natural-type streptokinase expression vector by the foregoing method, cleaving the vector with suitable restriction enzyme to remove a specific region, repairing the gene with a chemically synthesized oligonucleotide fragment having the desired base sequence, incorporating the gene into a suitable vector again similarly to construct the desired derivative protein expression vector, introducing the vector into host cells and incubating the cells. With this method, the amino acid residue at an optional position in the natural-type streptokinase of the formula (1) can be removed or replaced or a contemplated amino acid residue can be inserted in a desired position by procedures already described or to be described in detail in the examples to follow.

In this way, natural-type streptokinase and derivative protein thereof can be produced in large quantities with high purity and ease by gene engineering techniques. Especially, the streptokinase derivative protein obtained according to the invention is lower in antigenicity, more stable in blood and higher in the selectivity of thrombolytic activity and specificity thereof (thrombus selectivity) than natural-type streptokinase. The protein is therefore advantageously usable for medical applications wherein natural-type streptokinase is used.

EXAMPLES

Given below for a better understanding of the present invention are Examples 1 to 4 wherein natural-type streptokinase was prepared, and Examples 5 to 12 wherein streptokinase derivative proteins were prepared according to the invention.

The following drawings be referred to in the examples.

Figure 1:
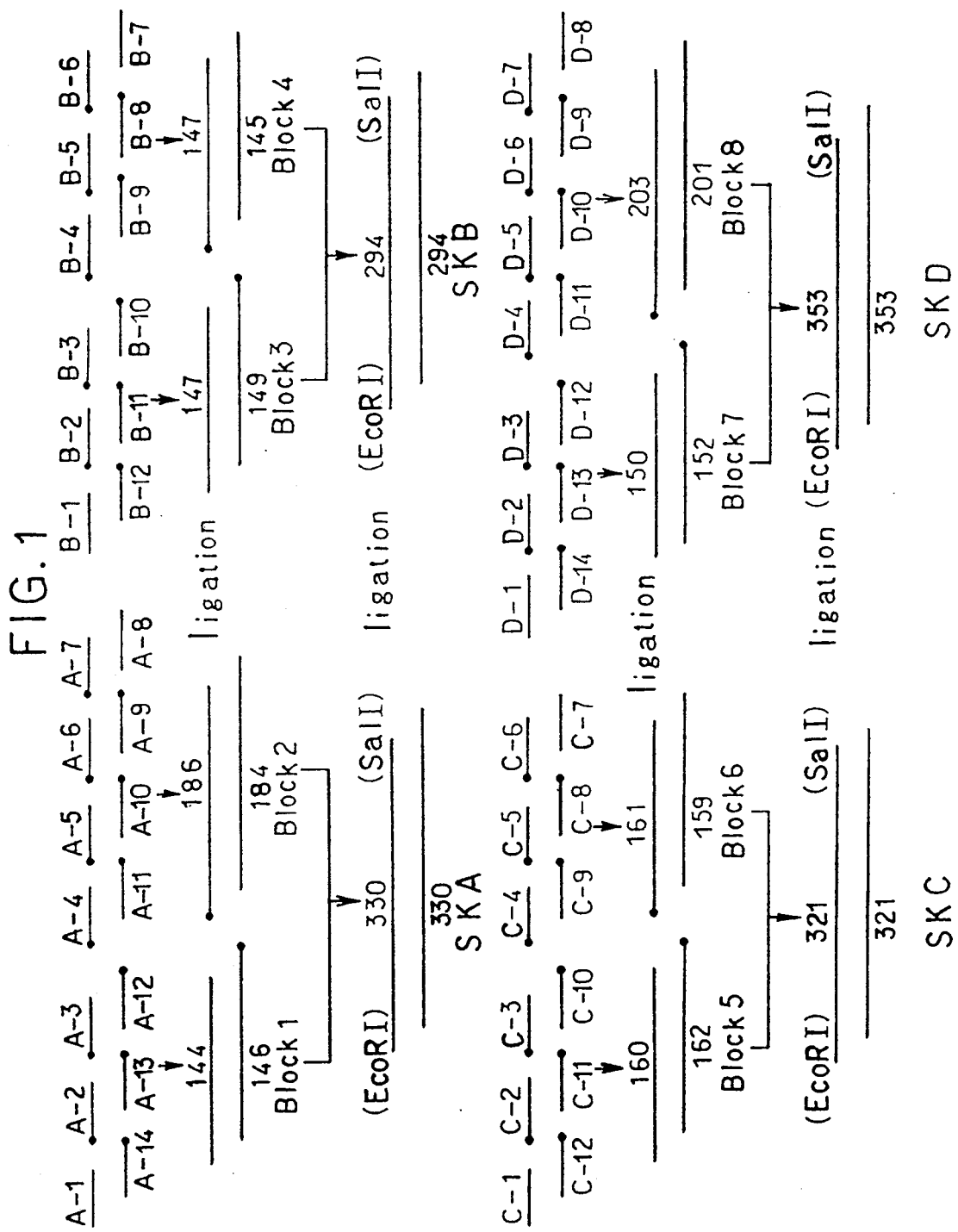
FIG. 1 is a diagram showing procedures in Example 1 for constructing block 1 to block 8 from synthetic oligonucleotides and for constructing streptokinase gene subunits SKA, SKB, SKC and SKD from the blocks.

The methods and procedures employed in Examples are as follows unless otherwise stated. 1. Cleavage of DNA with restriction enzymes The restriction enzymes used were those produced by Takara Shuzo Co., Ltd., Toyobo Co., Ltd. and Nippon Gene Co., Ltd. The mixtures to be reacted were those of compositions specified by the respective companies. For reaction, each mixture was allowed to stand in a water bath at 37° C. for 3 hours. As a standard, the restriction enzyme was used in an amount of one unit per microgram of DNA, such that the amount of reaction mixture eventually obtained was 100 μl. A sterilized 1.5-ml Eppendorf tube was used as the reactor.

2. Phenol extraction

This extraction method was practiced after the completion of the enzymatic reaction to inactivate the enzyme and terminate the reaction. To the reaction mixture was added TE-saturated phenol (phenol saturated with 10 mM tris-HCl (pH 8.0) containing 1 mM EDTA) in one-half the amount of the reaction mixture, followed by full stirring by shaking and then by centrifugation (12000 r.p.m., 5 minutes) to obtain an aqueous layer containing DNA. To the aqueous layer was added the same amount of ether, and the mixture was similarly stirred and centrifuged to collect an aqueous layer. This procedure was repeated two to three times. To the resulting aqueous layer were added 3 M sodium acetate buffer (pH 5.0) in 0.1 times the amount of the layer and cold ethanol in 2.5 times the amount of the layer. The mixture was stirred by shaking, then allowed to stand at −80° C. for at least 30 minutes and thereafter centrifuged (12000 r.p.m., 5 minutes), whereby the DNA was collected as a sediment.

3. Ligation of DNA fragments with T4 DNA ligase

The DNA was dissolved in an aqueous solution containing 67 mM tris-HCl (pH 7.6), 6.7 mM magnesium chloride, 10 mM dithiothreitol and 1 mM ATP, and T4 DNA ligase (product of Takara Shuzo Co., Ltd.) was added to the solution in an amount of one unit per microgram of DNA. The mixture was reacted at 12° C. for at least 5 hours or at 4° C. overnight to ligate the DNA fragments. The amount of reaction mixture finally obtained was 100 μl. After the reaction, the DNA was collected by the phenol extraction method.

4. Method of transformation $E.\ coli$, the strain HB-101 or JM-109 was used as the host cell.

The strain was incubated with shaking in L-broth medium (1% bacto trypton, 0.5% bacto yeast extract and 0.5% sodium chloride) at 37° C. until the absorbance at 600 nm reached 0.25. The culture (10 ml) was centrifuged (7000 r.p.m., 5 minutes) to collect the cells, which were then ice-cooled. The cells were suspended with addition of 5 ml of 0.1M magnesium chloride and washed, followed by centrifugation (7000 r.p.m., 1 minute) to collect the cells. A 5 ml quantity of ice-cooled mixture of 0.1M calcium chloride and 0.05M magnesium chloride was added to the cells to obtained a suspension, which was then allowed to stand in ice for at least 30 minutes and thereafter centrifuged (7000 r.p.m., 1 minute). The cells collected were suspended in 0.5 ml of the same solution again. To 0.2 ml of the suspension was added 20 μl of the reaction mixture of DNA ligated with T4 DNA ligase, and the mixture was ice-cooled for 30 minutes. Subsequently, the mixture was heated in a water bath at 42.5° C. for 30 seconds. With addition of 1.0 ml of L-broth medium, the mixture was allowed to stand in a water bath at 37° C. for 1 hour.

The transformant to be obtained was selected by the following procedure utilizing antibiotic resistance for identification, i.e., by spreading 0.2 ml portions of the reaction mixture over a plate medium prepared by adding 50 μg/ml of ampicillin to L-broth medium containing 1.5% agar, and allowing the mixture to stand overnight at 37° C. The active colonies were isolated.

5. Isolation and purification of plasmid

The strain harboring plasmids was incubated with shaking at 37° C. for 12 to 16 hours in 400 ml of L-broth medium containing 50 μg/ml of ampicillin. The culture was centrifuged (6000 r.p.m., 10 minutes) to collect the cells, to which was added 14 ml of solution I (50 mM glucose, 10 mM EDTA, 25 mM tris-HCl (pH 8.0) and 2 mg/ml of lysozyme, as sterilized) to obtained a suspension. The suspension was allowed to stand in ice for 30 minutes. With addition of 28 ml of solution II (0.2N sodium hydroxide and 1% sodium dodecylsulfate), the suspension was stirred and allowed to stand in ice for 5 minutes. A 21 ml quantity of solution III (3M sodium acetate (pH 4.8), as sterilized) was then added to the suspension, and the mixture was allowed to stand in ice for at least 60 minutes and thereafter centrifuged (8000 r.p.m., 10 minutes) to obtain a sediment. The sediment was dissolved in 11 ml of solution IV (0.1M sodium acetate and 0.05M tris-HCl (pH 8.0)), cold ethanol was added to the resulting solution in 2.5 times the amount thereof, and the mixture was allowed to stand at −80° C. for 30 minutes. The mixture was centrifuged again (12000 r.p.m., 15 minutes) to collect a sediment.

The sediment was dissolved in 4 ml of TE buffer (solution of 10 mM tris-HCl (pH 7.5) and 1 mM EDTA), 4.62 g of cesium chloride was dissolved in the solution with stirring, and 0.42 ml of ethidium bromide solution (5 mg/ml) was added. The combined solution was centrifuged (3000 r.p.m., 10 minutes) to remove the suspended matter, and the resulting solution was ultra-centrifuged (50000 r.p.m., for 15 hours). The resulting product was irradiated with ultraviolet rays to collect a plasmid DNA portion emitting fluorescence. This portion was subjected to extraction five to six times using isopropanol saturated with 5M sodium chloride solution to remove the ethidium bromide. Finally, the portion was subjected to Biogel A-50 (product of Bio Rad Laboratories) column chromatography (column size: 2.5 cm × 15-20 cm, eluent: TE buffer +0.5M sodium chloride solution, detection at UV 254 nm) to remove the cesium chloride and RNA and the like present. Plasmid DNA was collected by the phenol extraction method.

The amount of purified plasmid DNA was determined from $OD_{260\ nm}$ measurement, with $OD_{260}=0.022$ calculated as 1 μg/ml of DNA.

6. Synthesis of oligonucleotide

DNA was chemically synthesized using a DNA synthesizer, Model 381A type, product of Applied Biochemicals (solid-phase β-cyanoethyl phosphoamidide method, with use of 0.2 μM column). The procedure followed was according to the manufacturer's manual. The oligonucleotide obtained by the synthesizer has the column carrier resin attached to the 3' end, protective groups to the active groups, and dimethoxytrityl group to the 5' end, so that the resin and these groups need to be removed. The removal procedure was also according to the manual.

Next, HPLC was conducted until a single peak was obtained for fractionation and purification to separate the by-product, free protective groups and protective group removing agents from the desired oligonucleotide. The column used was YMCA-PACK AM-303 ODS (4.6×250 mm, Waters type, product of Yamamura Chemical Laboratories). Gradient elution was conducted using as eluents 5% to 40% acetonitrile/0.1M triethyl ammonium acetate aqueous solutions (pH 7.2). The system used had a pump CCPM, UV visible detector UV-8000 and controller CCP which were products of Tosoh Corporation.

7. Agarose gel electrophoresis

Agarose gel was used at a concentration of 0.9 or 1.6%. The agarose gel was prepared by weighing out an amount of Agarose I (product of Dojin Chemical Lab.) and dissolving the agarose in TBE buffer (containing 0.089M tris-boric acid and 0.02M EDTA) to the specified concentration with heating. Electrophoresis was performed using a mini gel electrophoresis system Mupid-2 (product of Cosmo-Bio Co., Ltd.) and TBE buffer as an electrophoretic buffer. The resulting gel was dipped in a solution of 0.5 μg/ml of ethidium bromide and observed under ultraviolet light to detect DNA fragments emitting fluorescence. The DNA was eluted from the gel by removing the desired band portions with a knife, placing the portions into a dialysis tube (3500 MW cut), filling the tube with TE buffer and electrophorescing the portions for 30 minutes using the same system as above. The DNA obtained was concentrated to dryness, a small amount of distilled water was added thereto, and the mixture was treated by the phenol extraction method to collect the DNA.

8. Analysis of base sequence

The base sequences of streptokinase and the protein of derivative thereof were analyzed by the M-13 dideoxy method [J. Messing., Methods in Enzymology, 101, 20 (1983)] using M-13 sequencing kit (with use of (α-32P) dCTP, product of Amersham International Ltd.) manufactured by Toyobo Co., Ltd. according to the manufacturer's manual. The sequencing gel used was FUJI GENSOR GEL SHEET (S0802, concentration 8%) manufactured by Fuji Photo Film Co., Ltd.

EXAMPLE 1

Preparation of Streptokinase Expression Vector pSKXT (1) Construction of pSKX

A detailed description will be given of the construction of plasmid pSKX which has incorporated therein a chemically synthesized gene of natural-type streptokinase by cloning.

1) Synthesis of Oligonucleotides

In constructing the whole base sequence represented by the formula (3) and including the structural gene of streptokinase, the base sequence was first divided into 52 oligonucleotide fragments (A-1 to A-14, B-1 to B-12, C-1 to C-12 and D-1 to D-14) having 43 to 56 bases and listed in Tables 1 to 4 below, and the individual fragments were chemically synthesized by the solid-phase β-cyanoethyl phosphoamidide method.

TABLE 1

| Fragment | Number | Base Sequence |
|---|---|---|
| A-1 | 47 | 5' AATTCGGATCCATGATCGCGGGCCCGGAAT GGCTGCTGGACCGTCCG 3' |
| A-2 | 49 | 5' TCTGTTAACAACTCCCAGCTGGTTGTTTCC GTAGCTGGCACTGTTGAAG 3' |
| A-3 | 48 | 5' GTACTAACCAGGACATCTCTCTGAAATTTT TCGAAATCGACCTGACCT 3' |
| A-4 | 46 | 5' CTCGTCCGGCCCATGGTGGTAAAACCGAAC AGGGCCTGTCCCCGAA 3' |
| A-5 | 46 | 5' ATCTAAACCGTTCGCTACTGACTCTGGCGC TATGTCTCATAAACTC 3' |
| A-6 | 46 | 5' GAGAAGGCAGATCTGCTGAAAGCAATCCAG GAACAGCTGATCGCTA 3' |
| A-7 | 48 | 5' ACGTACATTCTAACGACGACTACTTTGAGG TAATCGACTTCGCTAGCG 3' |
| A-8 | 43 | 5' TCGACGCTAGCGAAGTCGATTACCTCAAAG TAGTCGTCGTTAG 3' |
| A-9 | 47 | 5' AATGTACGTTAGCGATCAGCTGTTCCTGGA TTGCTTTCAGCAGATCT 3' |
| A-10 | 46 | 5' GCCTTCTCGAGTTTATGAGACATAGCGCCA GAGTCAGTAGCGAACG 3' |
| A-11 | 48 | 5' GTTTAGATTTCGGGGACAGGCCCTGTTCGG TTTTACCACCATGGGCCG 3' |
| A-12 | 45 | 5' GACGAGAGGTCAGGTCGATTTCGAAAAATT TCAGAGAGATGTCCT 3' |
| A-13 | 51 | 5' GGTTAGTACCTTCAACAGTGCCAGCTACGG AAACAACCAGCTGGGAGTTGT 3' |
| A-14 | 50 | 5' TAACAGACGGACGGTCCAGCAGCCATTCCG GGCCCGCGATCATGGATCCG 3' |

TABLE 2

| Fragment | Number | Base Sequence |
|---|---|---|
| B-1 | 49 | 5' AATTCGCTAGCCACGCTACTATCACCGACC GTAACGGCAAAGTATACTT 3' |
| B-2 | 49 | 5' CGCTGACAAAGACGGTTCTGTAACTCTTCC GACTCAACCGGTACAGGAA 3' |
| B-3 | 49 | 5' TTTCTGCTGTCTGGCCATGTACGCGTTCGC CCGTACAAAGAAAAACCGA 3' |
| B-4 | 49 | 5' TCCAGAACCAGGCTAAATCTGTTGACGTAG AATACACCGTTCAGTTCAC 3' |
| B-5 | 49 | 5' CCCGCTGAACCCAGACGATGACTTCCGCCC GGTCTGAAAGACACTAAA 3' |
| B-6 | 49 | 5' CTGCTGAAAACCCTGGCTATCGGTGACACC ATCACTTCTCAGGAGCTCG 3' |
| B-7 | 45 | 5' TCGACGAGCTCCTGAGAAGTGATGGTGTCA CCGATAGCCAGGGTT 3' |
| B-8 | 49 | 5' TTCAGCAGTTTAGTGTCTTTCAGACCCGGG CGGAAGTCATCGTCTGGGT 3' |
| B-9 | 51 | 5' TCAGCGGGGTGAACTGAACGGTGTATTCTA CGTCAACAGATTTAGCCTGGT 3' |
| B-10 | 47 | 5' TCTGGATCGGTTTTTCTTGTACGGGCGAA CGCGTACATGGCCAGAC 3' |

TABLE 2-continued

| Fragment | Number | Base Sequence |
| --- | --- | --- |
| B-11 | 49 | 5' AGCAGAAATTCCTGTACCGGTTGAGTCGGA AGAGTTACAGAACCGTCTT 3' |
| B-12 | 53 | 5' TGTCAGCGAAGTATACTTTGCCGTTACGGT CGGTGATAGTAGCGTCGCTAGCG 3' |

TABLE 3

| Fragment | Number | Base Sequence |
| --- | --- | --- |
| C-1 | 52 | 5' AATTCGAGCTCCTGGCTCAGGCACAGTCTA TCCTGAACAAAAACCATCCGGG 3' |
| C-2 | 54 | 5' CTACACTATCTACGAACGCGACTCTTCCAT CGTAACCCATGACAACGACATCTT 3' |
| C-3 | 54 | 5' CCGTACCATTCTGCCGATGGACCAGGAATT TACTTACCGTGTTAAAAACCGCGA 3' |
| C-4 | 53 | 5' ACAAGCTTACCGTATCAATAAAAAATCCGG TCTGAATGAAGAGATTAACAACA 3' |
| C-5 | 53 | 5' CTGACCTGATCTCTGAAAAGTACTACGTAC TGAAAAAAGGTGAGAAGCCGTAT 3' |
| C-6 | 55 | 5' GACCCGTTCGATCGTTCTCATCTGAAACTG TTCACCATCAAATACGTTGACGTCG 3' |
| C-7 | 51 | 5' TCGACGACGTCAACGTATTTGATGGTGAAC AGTTTCAGATGAGAACGATCG 3' |
| C-8 | 53 | 5' AACGGGTCATAAGGCTTCTCACCTTTTTTC AGTACGTAGTACTTTTCAGAGAT 3' |
| C-9 | 55 | 5' CAGGTCAGTGTTGTTAATCTCTTCATTCAG ACCGGATTTTTTATTGATACGGTAA 3' |
| C-10 | 52 | 5' GCTTGTTCGCGGTTTTTAACACGGTAAGTA AATTCCTGGTCCATCGGCAGAA 3' |
| C-11 | 54 | 5' TGGTACGGAAGATGTCGTTGTCATGGGTTA CGATGGAAGAGTCGCGTTCGTAGA 3' |
| C-12 | 56 | 5' TAGTGTAGCCCGGATGGTTTTTGTTCAGGA TAGACTGTGCCTGAGCCAGGAGCTCG 3' |

TABLE 4

| Fragment | Number | Base Sequence |
| --- | --- | --- |
| D-1 | 50 | 5' AATTCGACGTCGATACCAAGCAATTACTGA AGTCTGAGCAGCTGCTGACC 3' |
| D-2 | 50 | 5' GCTTCCGAACGTAATCTGGACTTCCGCGAT CTGTACGACCCGCGTGACAA 3' |
| D-3 | 50 | 5' AGCTAAACTGCTGTACAACAACCTGGATGC TTTCGGTATCATGGACTACA 3' |
| D-4 | 50 | 5' CCCTGACTGGTAAAGTAGAAGACAACCATG ACGACACCAACCGTATCATC 3' |
| D-5 | 50 | 5' ACCGTATACATGGGCAAACGTCCGGAAGGT GAAAATGCATCTTACCATCT 3' |
| D-6 | 50 | 5' GGCATATGACAAAGACCGTTACACCGAAGA AGAACGTGAAGTTTACTCTT 3' |
| D-7 | 53 | 5' ACCTGCGCTATACTGGTACCCCTATCCCGG ATAACCCGAACGATAAATAATAG 3' |
| D-8 | 49 | 5' TCGACTATTATTTATCGTTCGGGTTATCCG GGATAGGGGTACCAGTATA 3' |
| D-9 | 50 | 5' GCGCAGGTAAGAGTAAACTTCACGTTCTTC TTCGGTGTAACGGTCTTTGT 3' |
| D-10 | 50 | 5' CATATGCCAGATGGTAAGATGCATTTTCAC CTTCCGGACGTTTGCCCATG 3' |
| D-11 | 52 | 5' TATACGGTGATGATACGGTTGGTGTCGTCA TGGTTGTCTTCTACTTTACCAG 3' |
| D-12 | 48 | 5' TCAGGGTGTAGTCCATGATACCGAAAGCAT CCAGGTTGTTGTACAGCA 3' |
| D-13 | 50 | 5' GTTTAGCTTTGTCACGCGGGTCGTACAGAT CGCGGAAGTCCAGATTACGT 3' |
| D-14 | 54 | 5' TCGGAAGCGGTCAGCAGCTGCTCAGACTTC AGTAATTCGTTGGTATCGACGTCG 3' |

2) Ligation of Synthesized Oligonucleotides

The whole base sequence of the formula (3) was constructed as divided into subunits SKA, SKB, SKC and SKD.

Subunit SKA comprises, as shown by the following formula (5), a base sequence starting with EcoRI restriction enzyme recognition site of the whole base sequence, including ApaI and NheI restriction enzyme recognition sites and ending with SalI restriction enzyme recognition site. Subunit SKB comprises, as shown by the following formula (6), a base sequence starting with EcoRI restriction enzyme recognition site, including NheI and SacI restriction enzyme recognition sites and ending with SalI restriction enzyme recognition site. Subunit SKC comprises, as shown by the following formula (7), a base sequence starting with EcoRI restriction enzyme recognition site, including ScaI and AatII restriction enzyme recognition sites and ending with SalI restriction enzyme recognition site.

Subunit SKD comprises, as shown by the following formula (8), a base sequence starting with EcoRI restriction enzyme recognition site, including AatII restriction enzyme recognition site and ending with SalI restriction enzyme recognition site.

[Subunit SKA]
(EcoRI)                                                                                   (5)

```
              ←————————— A - 1 ——————————
5'   AATTCGGATCCATGATCGCGGGCCCGGAATGGCTGCTGGA
3'       GCCTAGGTACTAGCGCCCGGGCCTTACCGACGACCT
              ←————————— A - 14 —————————

——>< ——————————— A - 2 ——————————
     CCGTCCGTCTGTTAACAACTCCCAGCTGGTTGTTTCCGTA
     GGCAGGCAGACAATTGTTGAGGGTCGACCAACAAAGGCAT
        ——————————————————————————>< ——

——————————>< ——————— A - 3 ——————
     GCTGGCACTGTTGAAGGTACTAACCAGGACATCTCTCTGA
     CGACCGTGACAACTTCCATGATTGGTCCTGTAGAGAGACT
     ——————————— A - 13 ——————>< ——

——>< ———— A - 4 ——
     AATTTTTCGAAATCGACCTGACCTCTCGTCCGGCCCATGG
     TTAAAAAGCTTTAGCTGGACTGGAGAGCAGGCCGGGTACC
     ———— A - 12 ——————————>< ——

——>< ——————————
     TGGTAAAACCGAACAGGGCCTGTCCCCGAAATCTAAACCG
     ACCATTTTGGCTTGTCCCGGACAGGGGCTTTAGATTTGGC
     ——————— A - 11 ——————————>< ——

——————— A - 5 ——————————>< ——
     TTCGCTACTGACTCTGGCGCTATGTCTCATAAACTCGAGA
     AAGCGATGACTGAGACCGCGATACAGAGTATTTGAGCTCT
                  ——— A - 10 ————————

——————— A - 6 ———————
     AGGCAGATCTGCTGAAAGCAATCCAGGAACAGCTGATCGC
     TCCGTCTAGACGACTTTCGTTAGGTCCTTGTCGACTAGCG
     ——>< ——————————— A - 9 —————————

——>< ——————— A - 7 ——————————
     TAACGTACATTCTAACGACGACTACTTTGAGGTAATCGAC
     ATTGCATGTAAGATTGCTGCTGATGAAACTCCATTAGCTG
       ——>< ———————————— A - 8 —————

——>
     TTCGCTAGCG      3'
     AAGCGATCGCAGCT  5'
             ——>
                  (SalI)
```

[Subunit SKB]
(EcoRI)                                                                                   (6)

```
     ←——————— B - 1 ——————————
     AATTCGCTAGCGACGCTACTATCACCGACCGTAACGGCAA
         GCGATCGCTGCGATGATAGTGGCTGGCATTGCCGTT
     ←——————— B - 12 ————————

——>< —————— B - 2 ——————————
     AGTATACTTCGCTGACAAAGACGGTTCTGTAACTCTTCCG
     TCATATGAAGCGACTGTTTCTGCCAAGACATTGAGAAGGC
                  ——>< ———— B - 11 ——

——————>< ——————————
     ACTCAACCGGTACAGGAATTTCTGCTGTCTGGCCATGTAC
     TGAGTTGGCCATGTCCTTAAAGACGACAGACCGGTACATG
     ——————————————————————>< ——
```

```
―――――B - 3―――――――――→←――――――――――
GCGTTCGCCCGTACAAAGAAAAACCGATCCAGAACCAGGC
CGCAAGCGGGCATGTTTCTTTTTGGCTAGGTCTTGGTCCG
―――――――B - 10―――――――→←――――――――――

――――――――――B - 4―――――――――――→←―――
TAAATCTGTTGACGTAGAATACACCGTTCAGTTCACCCCG
ATTTAGACAACTGCATCTTATGTGGCAAGTCAAGTGGGGC
――――――――――――――――B - 9――――――――――――

――――――――――――B - 5―――――――――――――
CTGAACCCAGACGATGACTTCCGCCCGGGTCTGAAAGACA
GACTTGGGTCTGCTACTGAAGGCGGGCCCAGACTTTCTGT
――→←―――――――――B - 8――――――――――

―――→←―――――――――B - 6――――――――――
CTAAACTGCTGAAAACCCTGGCTATCGGTGACACCATCAC
GATTTGACGACTTTTGGGACCGATAGCCACTGTGGTAGTG
――――――→←――――――――B - 7―――――――――

―――――――――――→
TTCTCAGGAGCTCG
AAGAGTCCTCGAGCAGCT
――――――――――――――→

(SalI)

[Subunit SKC]
(EcoRI)                                                    (7)
    ←―――――――――C - 1―――――――――――
AATTCGAGCTCCTGGCTCAGGCACAGTCTATCCTGAACAA
    GCTCGAGGACCGAGTCCGTGTCAGATAGGACTTGTT
    ←―――――――――C - 12――――――――――

――――――――→←――――――――C - 2――――――――
AAACCATCCGGGCTACACTATCTACGAACGCGACTCTTCC
TTTGGTAGGCCCGATGTGATAGATGCTTGCGCTGAGAAGG
―――――――――――――→←――― C - 11 ―――――――

――――――――――――――――→←―――
ATCGTAACCCATGACAACGACATCTTCCGTACCATTCTGC
TAGCATTGGGTACTGTTGCTGTAGAAGGCATGGTAAGACG
                        ――――――――→←―――

――――――― C - 3 ―――――――――――――→
CGATGGACCAGGAATTTACTTACCGTGTTAAAAACCGCGA
GCTACCTGGTCCTTAAATGAATGGCACAATTTTTGGCGCT
―――――――――― C - 10―――――――――――

←―――――― C - 4 ―――――――
ACAAGCTTACCGTATCAATAAAAAATCCGGTCTGAATGAA
TGTTCGAATGGCATAGTTATTTTTTAGGCCAGACTTACTT
――→←―――――――― C - 9 ――――――――

―――――→←―――――― C - 5 ―――――――
GAGATTAACAACACTGACCTGATCTCTGAAAAGTACTACG
CTCTAATTGTTGTGACTGGACTAGAGACTTTTCATGATGC
―――――――――→←――― C - 8 ――――――――

――――――――――――――→←―――
TACTGAAAAAAGGTGAGAAGCCGTATGACCCGTTCGATCG
ATGACTTTTTTCCACTCTTCGGCATACTGGGCAAGCTAGC
                    ――――――――――→←―――

―――――――― C - 6 ―――――――――
TTCTCATCTGAAACTGTTCACCATCAAATACGTTGACGTC
AAGAGTAGACTTTGACAAGTGGTAGTTTATGCAACTGCAG
――――――――――― C - 7 ―――――――――
```

```
       →
       G
       CAGCT
            →
       (SalI)
```

[Subunit SKD]
(EcoRI)                                                          (8)

```
    ←─────────────────── D-1 ──────────────────────
    AATTCGACGTCGATACCAACGAATTACTGAAGTCTGAGCA
        GCTGCAGCTATGGTTGCTTAATGACTTCAGACTCGT
           ←─────────────── D-14 ────────────

────────────→←──────────── D-2 ──────────────
    GCTGCTGACCGCTTCCGAACGTAATCTGGACTTCCGCGAT
    CGACGACTGGCGAAGGCTTGCATTAGACCTGAAGGCGCTA
    ────────────────────→←────── D-13 ─────────

─────────────────────→←────────────────────
    CTGTACGACCCGCGTGACAAAGCTAAACTGCTGTACAACA
    GACATGCTGGGCGCACTGTTTCGATTTGACGACATGTTGT
                          →←──────────────────

───────── D-3 ────────────→←──────────────
    ACCTGGATGCTTTCGGTATCATGGACTACACCCTGACTGG
    TGGACCTACGAAAGCCATAGTACCTGATGTGGGACTGACC
    ───────────── D-12 ────────────→←─────────

───────────── D-4 ────────────────────────→
    TAAAGTAGAAGACAACCATGACGACACCAACCGTATCATC
    ATTTCATCTTCTGTTGGTACTGCTGTGGTTGGCATAGTAG
    ────────────────── D-11 ───────────────────

←────────────── D-5 ──────────────────────
    ACCGTATACATGGGCAAACGTCCGGAAGGTGAAAATGCAT
    TGGCATATGTACCCGTTTGCAGGCCTTCCACTTTTACGTA
    ────────→←──────── D-10 ──────────────────

────────────→←─────── D-6 ────────────────
    CTTACCATCTGGCATATGACAAAGACCGTTACACCGAAGA
    GAATGGTAGACCGTATACTGTTTCTGGCAATGTGGCTTCT
    ──────────────→←──── D-9 ─────────────────

──────────────────→←──────────────────────
    AGAACGTGAAGTTTACTCTTACCTGCGCTATACTGGTACC
    TCTTGCACTTCAAATGAGAATGGACGCGATATGACCATGG
    ────────────────────────→←────────────────

────────── D-7 ──────────────→
    CCTATCCCGGATAACCCGAACGATAAATAATAG
    GGATAGGGCCTATTGGGCTTGCTATTTATTATCAGCT
    ────────────── D-8 ─────────────→
```
(SalI)

The subunits were constructed as divided into blocks 1 to 8, which were constructed in the manner to be described below, as schematically shown in FIG. 1. With reference to FIG. 1, the solid dot at one end of the line representing a chemically synthesized oligonucleotide represents introduction of a phosphate group at the 5' end.

Of the 52 chemically synthesized oligonucleotides A-1 to D-14, the 44 oligonucleotides other than A-1, A-8, B-1, B-7, C-1, C-7, D-1 and D-8 were treated in the following manner to introduce the phosphate group into each oligonucleotide at the 5' end. A 20 μl quantity of 1 to 3 μg/ml solution of each oligonucleotide was prepared, 5 units of T4 DNA polynucleotidekinase (product of Takara Shuzo Co., Ltd.), 5 μl of reaction buffer specified by the company and 1 μl of 100 mM ATP were added to the solution, and the amount of the mixture was adjusted to 50 μl with addition of water. The mixture was then reacted at 37° C. for 1 hour.

Next, to DNA solutions (2 μl each) of oligonucleotides serving as the starting materials for each of the blocks to be constructed (e.g. oligonucleotides A-1, A-2, A-3, A-12, A-13 and A-14 in the case of block 1) were added 1 μl of 100 mM ATP and 10 μl of ligase reaction buffer (solution of 660 mM tris-HCl (pH 7.6), 66 mM magnesium chloride and 100 mM dithiothreithol), and the amount of mixture to be reacted was adjusted to 100 μl. The mixture was heated in a water bath at 100° C. for 2 minutes and thereafter cooled spontaneously. Subsequently, with addition 2.5 units of T4 DNA ligase (product of Takara Shuzo Co., Ltd.), the mixture was reacted at 4° C. overnight to ligate the nucleotides.

The ligated reaction product was subjected to phenol extraction and then to 10% polyacrylamide gel electrophoresis. A double-stranded portion which was the block of the desired size was removed from the gel and subjected to elution. Blocks 1 to 8 were constructed by the same procedure as above.

3) Preparation of pSKA, pSKB, pSKC and pSKD

Subunit SKA comprising block 1 and block 2 constructed by the procedure 2) was incorporated into plasmid pBR322 by the following procedure to obtain vector pSKA. Similarly, pSKB, pSKC and pSKD were prepared.

Figure 2:
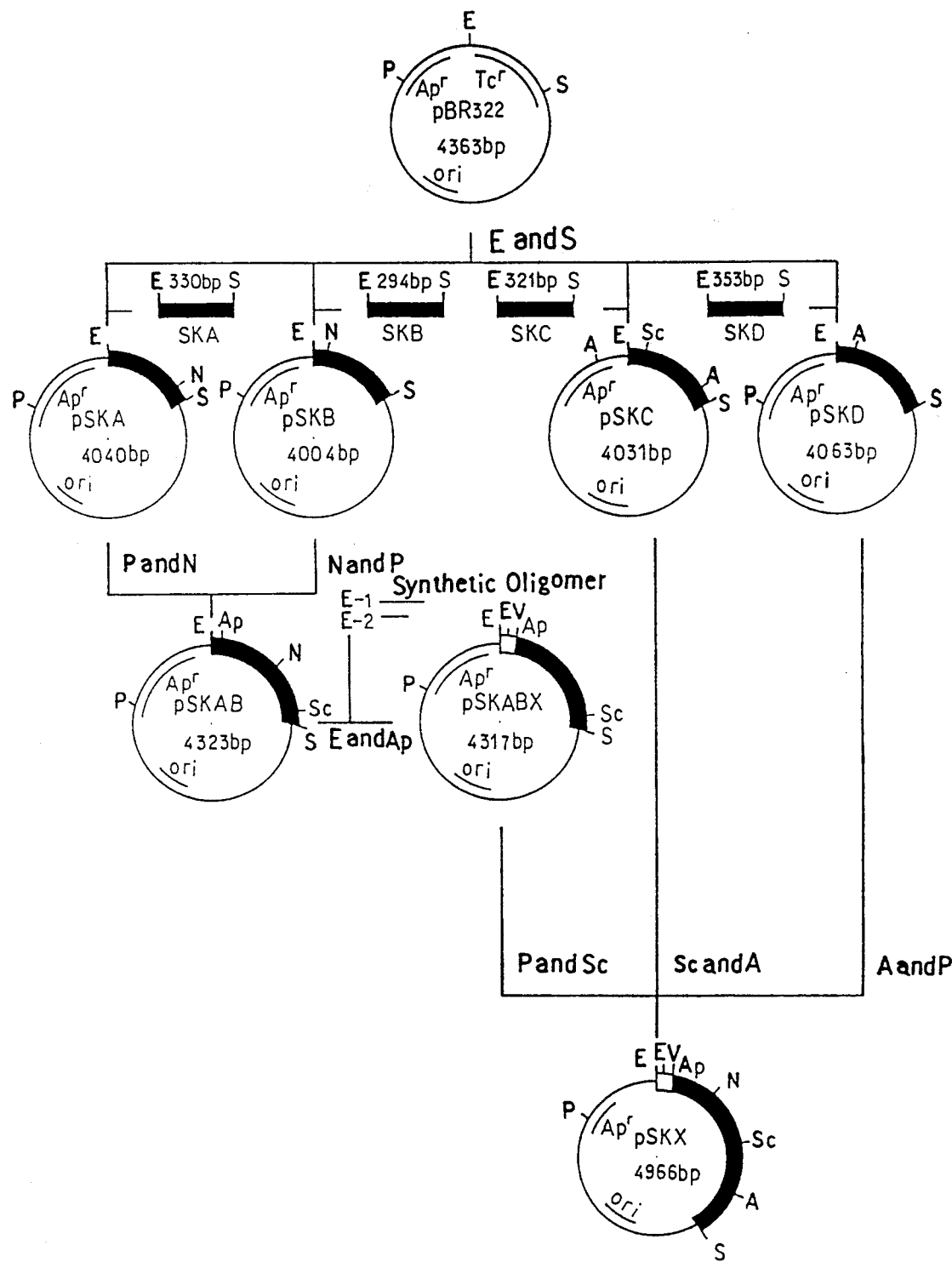
FIG. 2 is a diagram showing procedures in Example 1 for preparing plasmids pSKA, pSKB, pSKC and pSKD having the respective subunits and for preparing streptokinase cloning vector pSKX from these plasmids via plasmid vectors pSKAB and pSKABX.

FIG. 2 schematically shows the procedures. With reference to the diagram, Ap$^r$ stands for ampicillin resistance, Tc$^r$ for tetracycline resistance, and ori for a replication origin. The restriction enzyme recognition sites of base sequences are to be represented by the following symbols, the same as the diagrams to follow.

| | | |
|---|---|---|
| A ... AatII | Ap .. ApaI | B ... BamHI |
| E ... EcoRI | EV .. EcoRV | N ... NheI |
| Na .. NaeI | P ... PstI | S ... SalI |
| Sc .. SacI | | |

3)-1 Preparation of pSKA

First, pBR322 was treated with restriction enzymes EcoRI and SalI and then electrophoresed on 0.9% agarose gel to obtain a DNA fragment of about 3.7 kb. The DNA fragment was mixed with block 1 and block 2 prepared above, T4 DNA ligase, ATP and ligase reaction buffer, followed by reaction at 4° C. overnight to ligate DNA. E. coli HB-101 was transformed by the calcium method using the reaction mixture. DNA was collected from the colonies obtained by the simplified boiling method, followed by screening to select the colonies containing the desired pSKA. The alkali-SDS extraction method, CsCl equilibrium density ultracentrifugation method and Biogel A-50 column chromatography were further practiced to collect purified DNA, and a restriction enzyme cleavage map was prepared using restriction enzymes (EcoRI, BglII, ApaI, NcoI, SalI, XhoII, HinfI, etc.)

Consequently, it was confirmed that the colonies selected contained the desired pSKA.

Further the SKA introduction portion of pSKA was checked for base sequence by the M-13 dideoxy method. More specifically, EcoRI-SalI fragment was subcloned in Mm-13 mp18 or mp19 to analyze the base sequence. As a result, the desired sequence was identified.

3)-2 Preparation of pSKB, pSKC and pSKD

By the same procedure as the above 3)-1, E. coli HB-101 was transformed with subunit SKB comprising block 3 and block 4, followed by colony screening, and collection and purification of plasmid DNA, to prepare pSKB, which was similarly identified.

Similarly, subunit SKC comprising block 5 and block 6 was introduced in E. coli HB-101 for transformation, followed by screening of colonies, and collection and purification of plasmid DNA to prepare pSKC, which was identified similarly. E. coli HB-101 was likewise transformed with subunit SKD comprising block 7 and block 8, followed by screening of colonies, and collection and purification of plasmid DNA.

4) Preparation of pSKAB

This plasmid is an intermediate vector for constructing pSKX contemplated. The procedure for preparing the vector, which is schematically illustrated in FIG. 2, is as follows.

pSKA obtained by the procedure 3) was treated with restriction enzyme PstI and NheI and electrophoresced on agarose gel to isolate and purify a 1072 bp DNA fragment.

Similarly, pSKB obtained by the procedure 3) was treated with the same restriction enzymes as above to isolate and purify a 3250 bp DNA fragment.

The two DNA fragments were ligated with T4 DNA ligase, and E. coli HB-101 was transformed with the resulting reaction mixture to obtain colonies containing the desired pSKAB. Plasmid DNA was collected from the colonies and purified. pSKAB of 4323 bp was confirmed by restriction enzyme cleavage mapping.

5) Preparation of pSKABX

Construction of the streptokinase secreting expression vector requires a plasmid vector with a base sequence not having the codon for Met attached to the front of the first-position amino acid of streptokinase. Accordingly pSKABX was prepared by altering the N-terminal of pSKAB through the following procedure.

FIG. 2 shows the procedure schematically.

pSKAB was treated with restriction enzymes EcoRI and ApaI and ligated with oligonucleotides E-1 and E-2 freshly chemically synthesized, in the presence of T4 DNA ligase. E. coli was transformed with the reaction mixture, vector DNA was collected from the resulting colonies and purified, and a restriction enzyme cleavage map was prepared to obtain the desired pSKABX.

Given below are the base sequences of oligonucleotides E-1 and E-2 and of a linker obtained with use of these nucleotides for constructing the secreting expression vector.

| Linker | Number of of bases | Base sequence |
|---|---|---|
| E-1 | 18 | AATTCGATATCGCGGGCC |
| E-2 | 10 | CGCGATATCG |

Linker for constructing secreting expression vector

<u>AATT</u>CGATATCG<u>CGGGCC</u>
GCTATAGCGC
(EcoRI)          (ApaI)

The plasmid vector thus obtained can be used for constructing a system for secreting and expressing streptokinase. The E-1 and E-2 introducing portion of pSKABX was found to have the above base sequence by the M-13 dideoxy method [J. Messing, Methods in Enzymology, 101, 20 (1983)].

6) Preparation of pSKX

FIG. 2 schematically shows a procedure for preparing pSKX.

pSKABX was treated with restriction enzymes SacI and PstI to obtain a DNA fragment having 1352 bp, which was ligated with a DNA fragment of 309 bp obtained by treating pSKC with restriction enzymes SacI and AatII and a DNA fragment of 3305 pb obtained by treating pSKD with restriction enzymes AatII and PstI. E. coli was transformed with the reaction mixture, followed by the same procedures as above, i.e. collection and purification of vector DNA and restriction enzyme mapping.

The procedure revealed that the desired pSKX (4966 pb) was obtained.

EXAMPLE 2

Construction of Streptokinase Secreting Expression Vector

A vector was constructed for secreting and expressing streptokinase in the periplasm of E. coli. The chemically synthesized streptokinase gene was ligated to tac promoter and bla signal peptide so that the codon frame of the streptokinase structural gene would not be displaced from the codon stream of amino acid sequence of bla signal peptide, whereby the desired streptokinase secreting expression vector was constructed.

Figure 3:
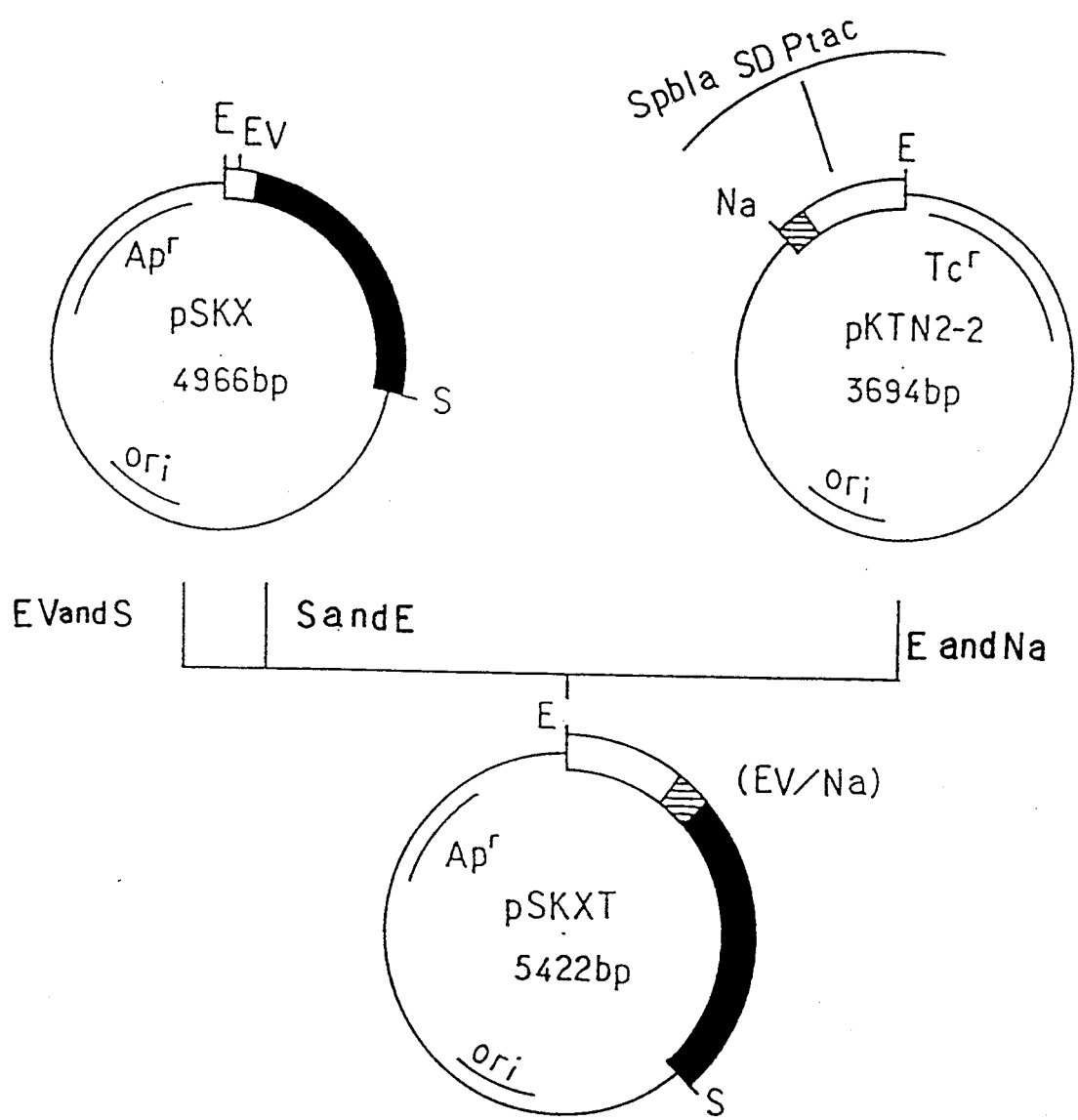
FIG. 3 is a diagram showing a procedure for preparing streptokinase secreting expression vector pSKXT from vector pSKX and plasmid pKTN2-2 in Example 2.

FIG. 3 shows the construction procedure. Same symbols as above were used for indicating restriction enzyme recognition sites. Spbla stands for bla signal peptide, SD for ribosomal binding site, and Ptac for tac promoter. tac promoter is represented by the blank area, bla signal peptide by the hatched area, and the base sequence coding for the streptokinase gene by the solid black area.

1) Preparation of pSKXT pSKX was treated with restriction enzymes EcoRV and SalI to obtain a DNA fragment with 1251 bp. Similarly, pSKX was treated with restriction enzymes EcoRI and SalI to obtain a DNA fragment with 3711 bp. pKTN2-2 having tac promoter and bla signal peptide portions was treated with restriction enzymes EcoRI and NaeI to obtain a DNA fragment with 460 bp. (E. coli JM-103 harboring pKTN2-2 has been deposited as FERM P-9146). These fragments were collected by agarose gel or polyacrylamide gel electrophoresis and reacted for ligation. E. coli JM-109 was then transformed with the resulting reaction mixture.

Vector DNA was collected from the colonies obtained, purified, followed by restriction enzyme cleavage mapping to obtain the desired vector pSKXT.

E. coli JM-109 harboring pSKXT produces within the cell the fused protein of bla signal peptide and streptokinase through the action of tac promoter, the fused protein is then transferred by the action of bla signal peptide to the inner membrane where the signal peptide is excised by protease present in the membrane, and streptokinase only is secreted in the periplasm between the inner membrane and the outer membrane.

EXAMPLE 3

Expression and Identification of Streptokinase

1) Incubation of E. coli JM-109 Harboring Streptokinase Secreting Expression Vector pSKXT E. coli JM-109 harboring vector pSKXT and obtained in Example 2 was incubated with shaking in the following manner using M-9 casamino acid liquid medium of the composition listed in Table 5 below.

TABLE 5

| Ingredient | Amount |
| --- | --- |
| Disodium phosphate | 5.8 g |
| Potassium dihydrogen phosphate | 3.0 g |
| Sodium chloride | 5.0 g |
| Ammonium chloride | 1.0 g |
| 1M calcium chloride* | 0.1 ml |
| 1M magnesium chloride* | 1.0 ml |
| Glucose* | 5.0 g |
| Casamino acid (product of Difco) | 5.0 g |
| L-proline | 50 mg |
| Vitamin B$_1$ | 1 mg |
| Water | amount needed to make 1 liter of medium |

Each asterisked ingredient was separately sterilized by autoclaving (at 121° C. for 15 minutes). When required, ampicillin sterilized by filtration was added to a final concentration of 50 μg/ml.

The culture (1 ml) prepared above was placed into a Sakaguchi flask containing 100 ml of the medium and incubated at 37° C. with reciprocating shaking. About 3 hours (OD$_{600}$=about 0.3) after the start of incubation, IPTG (isopropyl-$\beta$-D-thiogalactoside, product of Sigma) was added to the culture to a final concentration of 0.25 mg/ml, followed by further incubation.

2) Extraction of Desired Product from Cells

Incubation conducted under the above conditions was discontinued about 4 hours after the addition of IPTG, and fractions were obtained by the following steps.

First, the culture was centrifuged (5000 r.p.m., 10 minutes) to separate cells and culture supernatant. The supernatant thus obtained will be referred to as the "medium fraction".

The cells obtained were suspended in 30 mM tris-HCl (pH 8.0)-20% sucrose buffer in the same amount as the culture, EDTA aqueous solution was added to the suspension to a final concentration of 0.01M, and the mixture was stirred by a rotary shaker at 24° C. at 180 r.p.m. for 10 minutes and then centrifuged (6000 r.p.m., 10 minutes). The resulting supernatant will be referred to as the "sucrose buffer fraction".

The sediment resulting from the centrifugation was suspended again in ice-cooled water in the same amount as the culture, and the suspension was allowed to stand in ice for 15 minutes with occasional stirring and thereafter centrifuged (10000 r.p.m., 5 minutes). The resulting supernatant will be referred to as the "periplasm fraction".

3) Determination of Streptokinase Activity

The plasminogen activator activity of the streptokinase was determined by measuring the activity of plasmin produced by the plasminogen activation of the streptokinase by the method of Jackson et al. [K. W. Jackson et al, Methods in Enzymology, 80, 387 (1981)].

The activity of plasmin was measured using a synthetic substrate, i.e., S-2251 (D-Val-Leu-Lys-p-nitroaniline, product of Kabi Vitrum), that is, by determining p-nitroaniline released by plasmin in terms of an increase in the absorbance at 405 nm, as will be described in detail below.

The specimen was diluted with 0.025% aqueous solution of Triton X-100, a 25 µl portion of the dilution and 25 µl of 50 mM tris-HCl buffer (pH 7.5) were placed into a test tube, and the mixture was incubated at 37° C. for 5 minutes. Human plasminogen (product of Sigma) was diluted with 50 mM tris-HCl buffer (pH 7.5) containing mg/ml of bovine serum albumin (BSA) to a concentration of 80 µg/ml. The diluted human plasminogen (25 µl ) was placed into the test tube, and the mixture was incubated at 37° C. Fifteen minutes thereafter, 25 µl of S-2251 diluted to 2.5 mg/ml with 50 mM tris-HCl buffer (pH 7.5) containing 1.6M sodium chloride was added to the culture, followed by incubation at 37° C. for 10 minutes. The reaction was then terminated by addition of 1.5 ml of 0.2M acetic acid aqueous solution, and the absorbance of the culture was measured at 405 nm.

The activity unit of the specimen was determined with reference to a standard curve for a standard substance, i.e., streptokinase derived from *streptococcus equisimilis* H46A (Group C) and having specific activity of 100 international units/µg, the curve being obtained by using the standard substance in the same manner as above.

4) Western Blotting

The streptokinase present in the cells obtained by the procedure 2) above was detected by the Western blotting method [H. Towbin, T. Staehelin and J. Gordon, Proc. Natl. Acad. Sci., U.S.A., 76, 4350 (1979)] using streptokinase-specific antibody as will be described below in detail.

Streptokinase-specific anti-serum was prepared by immunizing rabbits with purified streptokinase derived from *Streptococcus equisimilis* H46A (Group C) as an antigen, i.e., by dissolving 1 mg of freeze-dried streptokinase in 0.5 ml of physiological saline, adding 0.5 ml of Freunds complete adjuvant to the solution to emulsify the streptokinase, subcutaneously giving the emulsion to the back of three rabbits, similarly giving the emulsified streptokinase at the same dose every two weeks to thus immunize the rabbits four times in total, collecting the total blood 10 days after the final immunization and separating off the serum. The anti-serum thus obtained was used for detecting streptokinase.

A specimen for polyacrylamide gel electrophoresis to be performed in the presence of sodium dodecylsulfate (hereinafter referred to as "SDS-PAGE") was prepared, for example, by suspending cells obtained from ml of culture in 1 ml of 10 mM tris-HCl buffer (pH 8.0) containing 2% SDS and 2% dithiothreitol, heating the suspension at 100° C. for 5 minutes and the centrifuging the suspension (12000 r.p.m., 10 minutes) to obtain a supernatant.

SDS-PAGE was performed by electrophoresing the specimen thus prepared at 2 mA/cm on 15% polyacrylamide containing 0.1% of SDS according to the Laemmli method U. K. Laemmli, Nature, 227, 680 (1970)]. The streptokinase was detected by electrophoretically transferring to a nitrocellulose film (product of Bio Rad) the protein in the resulting gel and specifically staining the streptokinase in the protein with use of specific antibody.

For the staining, the nitrocellulose film having the protein transferred thereto was shaken at room temperature for 1 hour in a 10% solution of bovine serum albumin (BSA) in 20 mM tris-HCl buffer (pH 7.5, hereinafter referred to briefly as "TBS") containing 0.15M sodium chloride and then reacted, at room temperature for 3 hours, with the streptokinase anti-serum as diluted to 1000-fold with 0.1% BSA-TBS. The resulting reaction mixture was washed with TBS four times and treated for 60 minutes with peroxidase-bound anti-rabbit IgG (product of Cappel) as diluted to 2000-fold with 0.1% BSA-TBS. The resulting mixture was washed again and thereafter treated with 0.02M citric acid buffer (pH 6.5) containing 0.03% hydrogen peroxide and 0.5 mg/ml 4-chloro-1-naphthol for color development.

5) Determination of Amount of Streptokinase Expressed

*E. coli* JM-109 harboring secreting expression vector pSKXT was incubated and fractionated by the procedures 1) and 2) above and checked by the procedure 3) to determine the amount of streptokinase expressed.

Consequently, no activity was detected from the medium supernatant fractions but 200 international units/ml of activity was detected from the cell fraction, i.e., almost entirely from the periplasm fraction. Further when analyzed by the procedure 4) above, the immunoactivity appeared at the position of about 47000 in molecular weight the same as in the case of natural type.

These results indicate that the streptokinase detected by the invention is the same as natural-type streptokinase and was produced by translation within the cell, then passed through the inner membrane by the action of the signal peptide, further processed for the removal of the signal peptide and secreted.

EXAMPLE 4

Preparation and Identification of Recombinant Streptokinase

1) Extraction from Cells

A 2.4-liter quantity of culture obtained by the incubation method of Example 3, 1) was centrifuged (8000 r.p.m., 10 minutes) to collect the cells, which were treated by the osmotic shock method described in Example 3, 2) to obtain a periplasm fraction.

2) Purification of streptokinase

Streptokinase can be collected from the extract of the fraction by a combination of separating methods such as salting-out with ammonium sulfate, isoelectric focusing, gel filtration, ion-exchange chromatography and hydrophobic chromatography, whereby a single purified product can be obtained. As an example, the combination of hydrophobic chromatography and anion-exchange chromatography will be described below.

First, ammonium sulfate was added to 600 ml of the periplasm fraction to a concentration of 0.6M, and the mixture was passed through a Butyl Toyo pearl column (3×20 cm, product of Tosoh Corporation) equilibrated with 0.6M ammonium sulfate. After washing the column with 500 ml of 0.3M ammonium sulfate, 50 mM tris-HCl buffer (pH 8.5) was passed through the column to elute a fraction having streptokinase activity. The fraction was then dialyzed against 50 mM tris-HCl buffer (pH 8.5), and the dialyzate was separated by a fractionating HPLC system (Model HLC-837, product of Tosoh Corporation) including DEAE-5PW (2.15×15 cm, product of Tosoh Corporation) at a flow rate of 4 ml/min using 50 mM tris-HCl buffer (pH 8.5) as an eluent at a straight concentration gradient of 0.1M to 0.3M sodium chloride. The Butyl Toyo pearl eluate fraction after dialyzation was injected into the HPLC system, and the main protein peak portion was pooled. The streptokinase activity fraction was eluted at a peak in match with the protein peak. The active eluate fraction pooled was further desalted by Sephadex G-25 column (2.5×25 cm, product of Pharmacia) and then separated again by a DEAE-5PW column under the same condition as above. Finally, the streptokinase active fraction was desalted by the same Sephadex G-25 column and lyophilized to obtain a final purified product.

3) Identification of Final Purified Product

3)-1 Measurement of Molecular Weight by SDS-PAGE

A sample of the purified product obtained by the procedure 2) was analyzed by SDS-PAGE in the presence of and also in the absence of a reducing agent.

Consequently, the sample exhibited a single band at the position of 47300 in molecular weight the same as the streptokinase derived from *Streptococcus equisimilis* H46A (Group C).

3)-2 Amino Acid Analysis

With addition of 6N hydrochloric acid, a sample of the purified product was hydrolyzed at 110° C. for 24 hours and subjected to amino acid analysis by the ninhydrin method using an automatic amino acid analyzer, Model Hitachi 835.

Table 6 below shows the result. For comparison, Table 6 also shows the result obtained by similarly analyzing the streptokinase derived from *Streptococcus equisimilis* H46A (Group G) (designated as "Natural" in Table 6.

TABLE 6

| Amino acid | Natural | Recombinant | Calculated |
|---|---|---|---|
| Asp | 65.5 | 63.8 | 65 |
| Thr | 29.4 | 29.2 | 30 |
| Ser | 23.6 | 23.0 | 25 |
| Glu | 46.1 | 45.4 | 44 |
| Pro | 21.2 | 22.6 | 21 |
| Gly | 20.8 | 20.4 | 20 |
| Ala | 21.9 | 21.6 | 21 |
| Val | 21.5 | 21.1 | 23 |
| ½ Cys | Not detected | Not detected | 0 |
| Met | 3.6 | 3.6 | 4 |
| Ile | 20.8 | 21.0 | 23 |
| Leu | 38.2 | 38.6 | 39 |
| Tyr | 22.1 | 21.3 | 22 |
| Phe | 15.2 | 15.1 | 15 |
| Trp | Not detected | Not detected | 1 |
| Lys | 32.4 | 32.2 | 32 |
| His | 8.8 | 9.0 | 9 |
| Arg | 19.8 | 19.9 | 20 |

3)-3 Analysis of Amino Acid Sequence

The Sequence of 20 amino acid residues at the amino end of a sample of the purified product was analyzed by the method of Heiwick et al. [R. M. Heiwick et al., J. Biol. Chem., 256, 7990 (1981)].

Consequently, the sequence of 20 amino acid residues at the amino end of the sample was found identical with that of the streptokinase (natural type) derived from *Streptococcus equisimilis* H46A It was possible for the above analysis procedure to identify Trp which was the sixth amino acid residue from the N-terminal and which was not detectable by the amino acid analysis procedure 3)-2 above.

The amount of recombinant streptokinase collected by the foregoing method was found to be 2.5 mg by the amino acid analysis of the final purified product sample.

The specific plasminogen activator activity was 101.5 international units/$\mu$g, which was comparable to that (100 international units/$\mu$g) of the natural type.

These results revealed that the streptokinase obtained was identical with the streptokinase (of the natural type) derived from *Streptococcus equisimilis* H46A (Group C).

EXAMPLE 5

Figure 4:
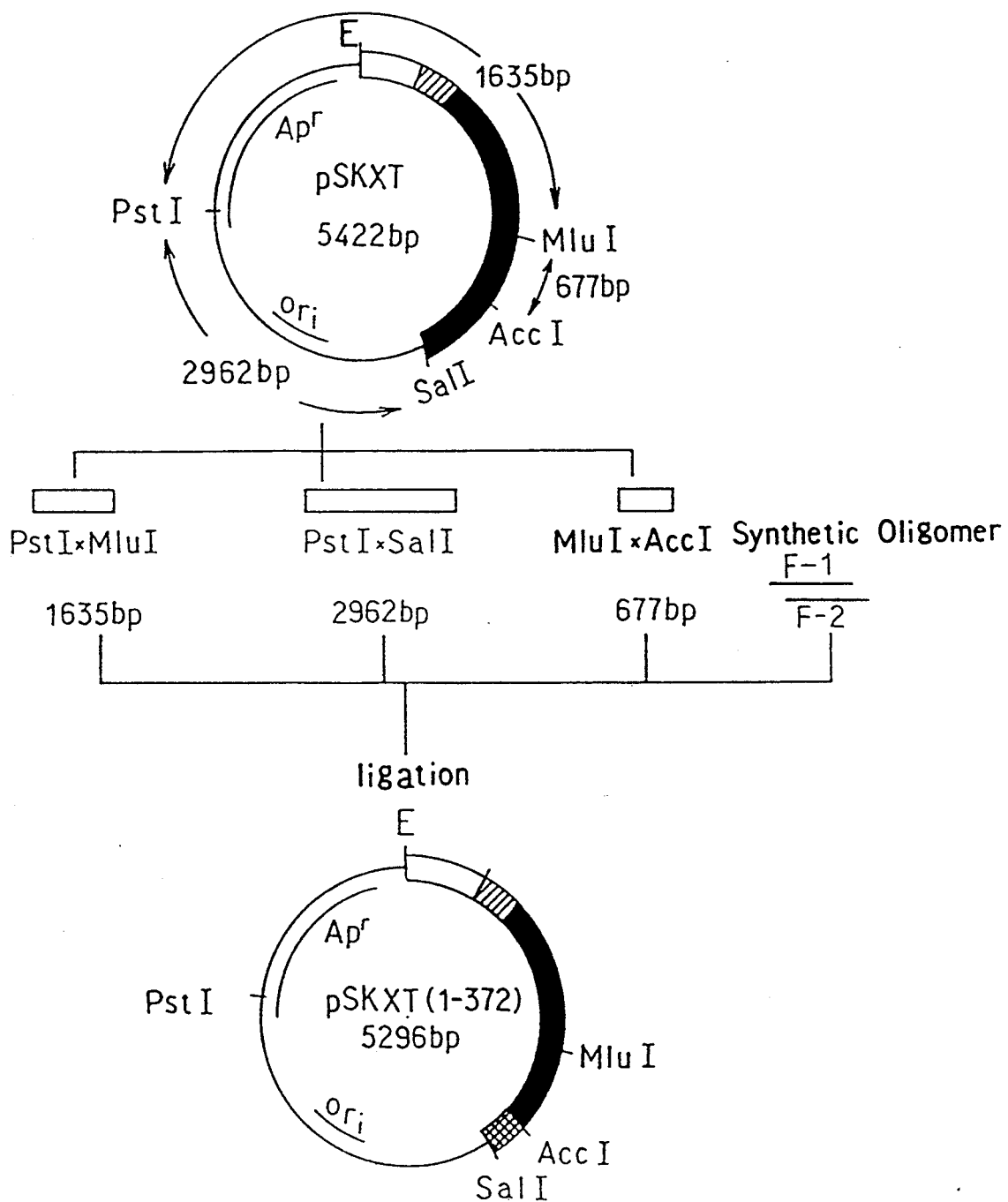
FIG. 4 is a diagram showing a procedure for preparing streptokinase derivative protein (1-372) expression vector in Example 5.

Preparation of Streptokinase Derivative Protein Expression Vector pSKXT (1-372) and Expression of the Protein A streptokinase derivative protein (1-372) expression vector was prepared by the following procedure using streptokinase expression vector pSKXT obtained in Example 2. FIG. 4 schematically shows the procedure.

1) Chemical Synthesis of DNA Fragments

For the preparation of a streptokinase derivative protein corresponding to streptokinase wherein amino acid residues toward the C-terminal are deficient, the following freshly chemically synthesized oligonucleotide (DNA) fragments F-1 and F-2 were used.

```
              F-1
     ATACATGGGCAAACGTTAATAG
         TGTACCCGTTTGCAATTATCAGCT
(Acc I)          F-2           (Sal I)
```

These DNA fragments were prepared by the same method as already described.

The vector for expressing the derivative protein was prepared by removing fragments having restriction enzyme recognition site AccI (present at the 367-position of streptokinase and at three other positions) and restriction enzyme recognition site SalI (present downstream from the termination codon of streptokinase and at another position) from pSKXT, and inserting the fragments F-1 and F-2 into the plasmid.

2) Construction of pSKXT (1-372)

pSKXT was treated with restriction enzymes PstI and MluI to obtain a DNA fragment of 1635 bp, with restriction enzymes PstI and SalI to produce a DNA fragment of 2962 bp, and further with restriction enzymes AccI and MluI to produce a DNA fragment of 677 bp. These fragments were collected by agarose gel electrophoresis and reacted with the chemically synthesized DNA fragment obtained by the procedure 1) above for ligation. *E. coli* JM109 was transformed with the reaction mixture, vector DNA collected from the resulting colonies and purified, and a restriction enzyme map was prepared to obtain the desired vector pSKXT (1-372).

3) Expression and Recognition of Derivative Protein (1-372)

*E. coli* JM-109 harboring vector pSKXT (1-372) obtained by the procedure 2) was incubated with shaking in the same manner as in Example 3, 1) using M-9 casamino acid liquid medium of the composition listed in Table 5.

About 4 hours after the addition of IPTG, incubation was discontinued, and the culture was separated into cells and a culture supernatant in the same manner as in Example 3, 2), and a sucrose buffer fraction and periplasm fraction were obtained.

In the same manner as in Example 3, 3) and 4), the fractions were checked for streptokinase activity and subjected to Western blotting, and the amount of expression of protein was determined.

Consequently, no activity was detected from the medium supernatant but expression of about 1000 international units/ml was detected from the cell fraction, i.e. almost entirely from the periplasm fraction. Further analysis by Western blotting revealed the immunoactivity at the position of calculated molecular weight of about 42300.

These results indicate that the streptokinase derivative protein (1-372) was produced by translation within the cell, then passed through the inner membrane by the action of the signal peptide, further processed for the removal of the signal peptide and secreted.

4) Preparation and Identification of Recombinant Streptokinase Derivative Protein (1-372)

In the same manner as in the procedure 3), 2.4 liters of culture was centrifuged (8000 r.p.m., 10 minutes) to collect the cells, from which a periplasm fraction was extracted by the osmotic shock method. Streptokinase derivative protein (1-372) was collected from the extract and purified in the same manner as in Example 4, 2) and finally lyophilized to obtain a purified product.

When analyzed by SDS-PAGE in the presence of a reducing agent, the purified product exhibited a single band at the position of contemplated molecular weight of about 42300.

With addition of 6N hydrochloric acid, the purified product was hydrolyzed at 110° C. for 24 hours and subjected to amino acid analysis by the ninhydrin method using the automatic amino acid analyzer, Model Hitachi 835. Table 7 below shows the result.

TABLE 7

| Amino acid | Purified product | Calculated |
|---|---|---|
| Asp | 56.6 | 58 |
| Thr | 25.9 | 27 |
| Ser | 20.8 | 23 |
| Glu | 39.5 | 38 |
| Pro | 18.5 | 17 |
| Gly | 18.4 | 18 |
| Ala | 19.4 | 19 |

TABLE 7-continued

| Amino acid | Purified product | Calculated |
|---|---|---|
| Val | 20.3 | 22 |
| ½ Cys | Not detected | 0 |
| Met | 3.6 | 4 |
| Ile | 19.9 | 22 |
| Leu | 36.3 | 37 |
| Tyr | 15.8 | 16 |
| Phe | 15.0 | 15 |
| Trp | Not detected | 1 |
| Lys | 30.2 | 30 |
| His | 7.7 | 8 |
| Arg | 16.7 | 17 |

The sequence of 20 amino acid residues from the amino end of the purified product was analyzed by the method of Heiwick et al., and the sequence of 5 residues from the carboxyl terminal thereof was analyzed with use of carboxypeptidases A and B. As a result, the product was identified as the desired streptokinase derivative protein (1-372).

The amount of recombinant streptokinase derivative protein (1-372) obtained by the above method was found to be 9 mg by the amino acid analysis of a sample of the purified product.

The specific plasminogen activator activity was 107 in mole ratio based on that of the natural-type streptokinase which was taken as 100 and was comparable to that of the natural type.

EXAMPLE 6

Figure 5:
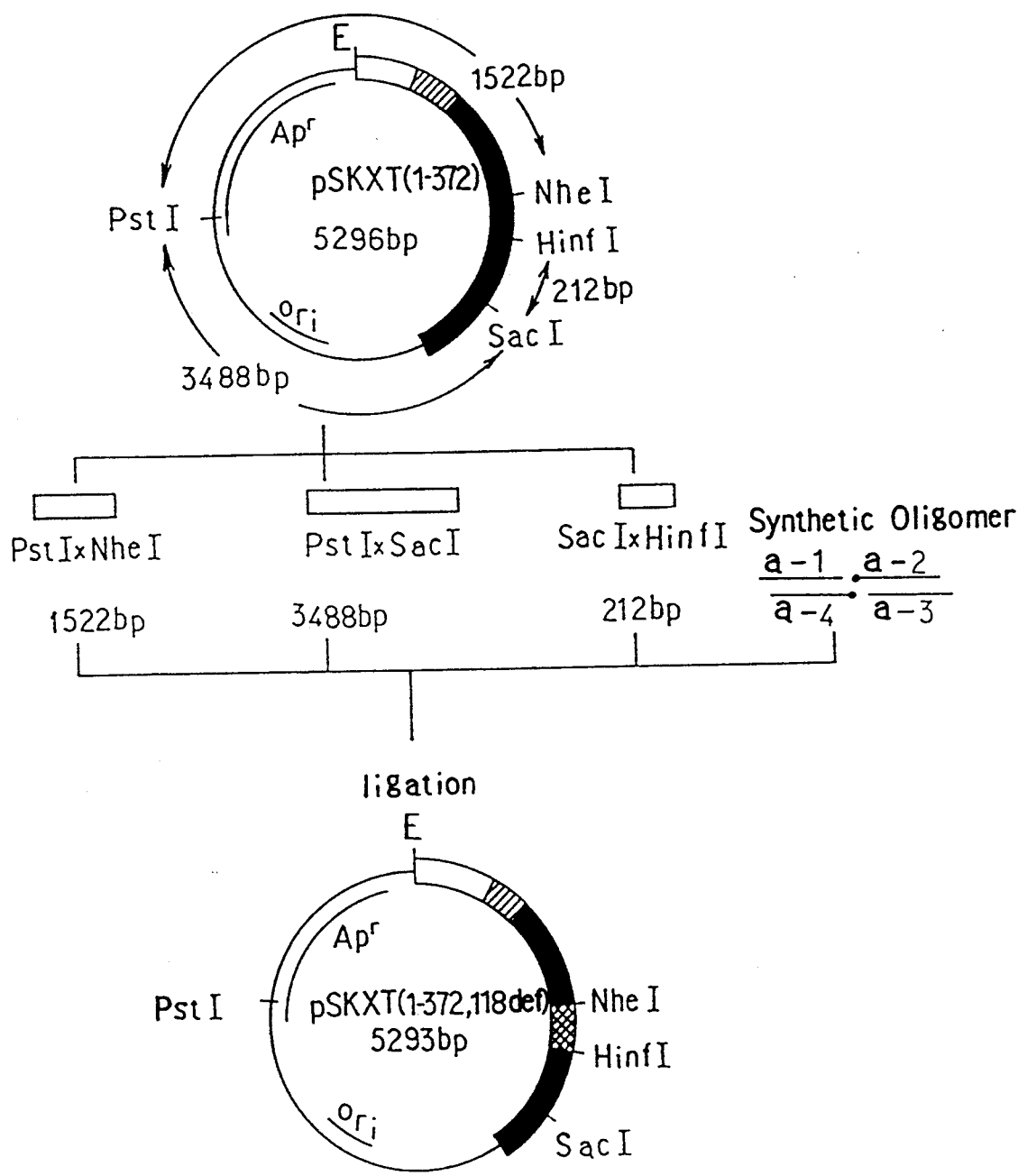
FIG. 5 is a diagram showing a procedure for preparing a vector for expressing streptokinase derivative protein (1-372, 118 deficient) in Example 6.

Preparation of Streptokinase Derivative Protein Expression Vector pSKXT (1-372, 118 Deficient) and Expression of the Protein A vector for expressing a streptokinase derivative protein (1-372, 118 deficient) was prepared by the following procedure using streptokinase derivative expression vector pSKXT (1-372) obtained in Example 5. FIG. 5 schematically shows the procedure. The desired vector is shown as "pSKXT (1-372, 118 def)" in the figure.

1) Chemical Synthesis of DNA Fragments

The desired derivative protein expression vector was prepared by replacing the sequence of pSKXT (1-372) between restriction enzyme recognition sites NheI and HinfI by the following freshly chemically synthesized oligonucleotide (DNA) fragments a-1 to a-4.

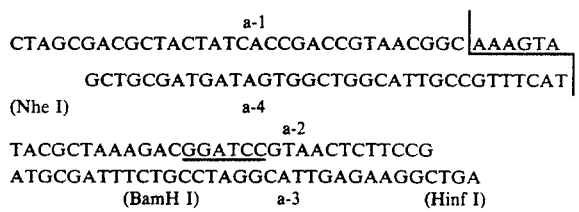

These DNA fragments were chemically prepared individually in the same manner as already stated. For the analysis to be performed later, restriction enzyme recognition site BamHI was provided which was not present in pSKXT (1-372).

2) Construction of pSKXT (1-372, 118 Deficient)

pSKXT (1-372) was treated with restriction enzymes PstI and NheI to form a DNA fragment of 1522 bp, with restriction enzymes PstI and SacI to form a DNA fragment of 3488 bp and further with restriction enzymes SacI and HinfI to form a DNA fragment of 212 bp. These fragments were collected by agarose gel electrophoresis and reacted with the four DNA fragments chemically synthesized by the procedure 1) above for ligation. (Oligomers a-2 and a-4 were used as phosphorylated at their 5 ends). *E. coli* JM109 was transformed with the reaction mixture, vector DNA was collected from the resulting colonies and purified, and a restriction enzyme map was prepared to obtain the desired vector pSKXT (1-372, 118 deficient).

3) Expression and Recognition of Derivative Protein (1-372, 118 Deficient)

*E. coli* JM109 harboring vector pSKXT (1-372, 118 deficient) obtained by the procedure 2) was incubated with shaking in the same manner as already stated using the same M-9 casamino acid liquid medium as above.

After the addition of IPTG, the cells were collected and checked for streptokinase activity (plasminogen activator activity) similarly. As a result, no activity was detected from the medium supernatant but expression of about 250 international units/ml was detected from the cell fraction, i.e., almost entirely from the periplasm fraction. Further analysis by Western blotting revealed the immunoactivity at the position of calculated molecular weight of about 42200.

4) Preparation and Identification of Recombinant Streptokinase Derivative Protein (1-372, 118 Deficient)

In the same manner as in Example 5, 4), 1.6 liters of culture was centrifuged to collect the cells, from which a periplasm fraction was extracted by the osmotic shock method. The desired derivative protein (1-372, 118 deficient) was collected from the extract and purified.

When analyzed by SDS-PAGE in the presence of a reducing agent, the purified product exhibited a single band at the position of contemplated molecular weight of about 42200.

With addition of 6N hydrochloric acid, the purified product was hydrolyzed at 110° C. for 24 hours and subjected to amino acid analysis by the ninhydrin method using the automatic amino acid analyzer, Model Hitachi 835. Table 8 below shows the result.

TABLE 8

| Amino acid | Purified product | Calculated |
|---|---|---|
| Asp | 57.7 | 58 |
| Thr | 26.5 | 27 |
| Ser | 21.7 | 23 |
| Glu | 39.0 | 38 |
| Pro | 17.4 | 17 |
| Gly | 19.1 | 18 |
| Ala | 19.7 | 19 |
| Val | 19.8 | 22 |
| ½ Cys | Not detected | 0 |
| Met | 3.3 | 4 |
| Ile | 20.1 | 22 |
| Leu | 37.5 | 37 |
| Tyr | 15.4 | 16 |
| Phe | 14.0 | 14 |
| Trp | Not detected | 1 |
| Lys | 30.0 | 30 |
| His | 7.9 | 8 |
| Arg | 16.5 | 17 |

The amount of recombinant streptokinase derivative protein (1-372, 118 deficient) obtained by the above method was found to be 2.4 mg by the amino acid analysis of a sample of the purified product.

The specific plasminogen activator activity was 100 in mole ratio based on that of the natural-type streptokinase which was taken as 100 and was equivalent to that of the natural type.

EXAMPLE 7

Figure 6:
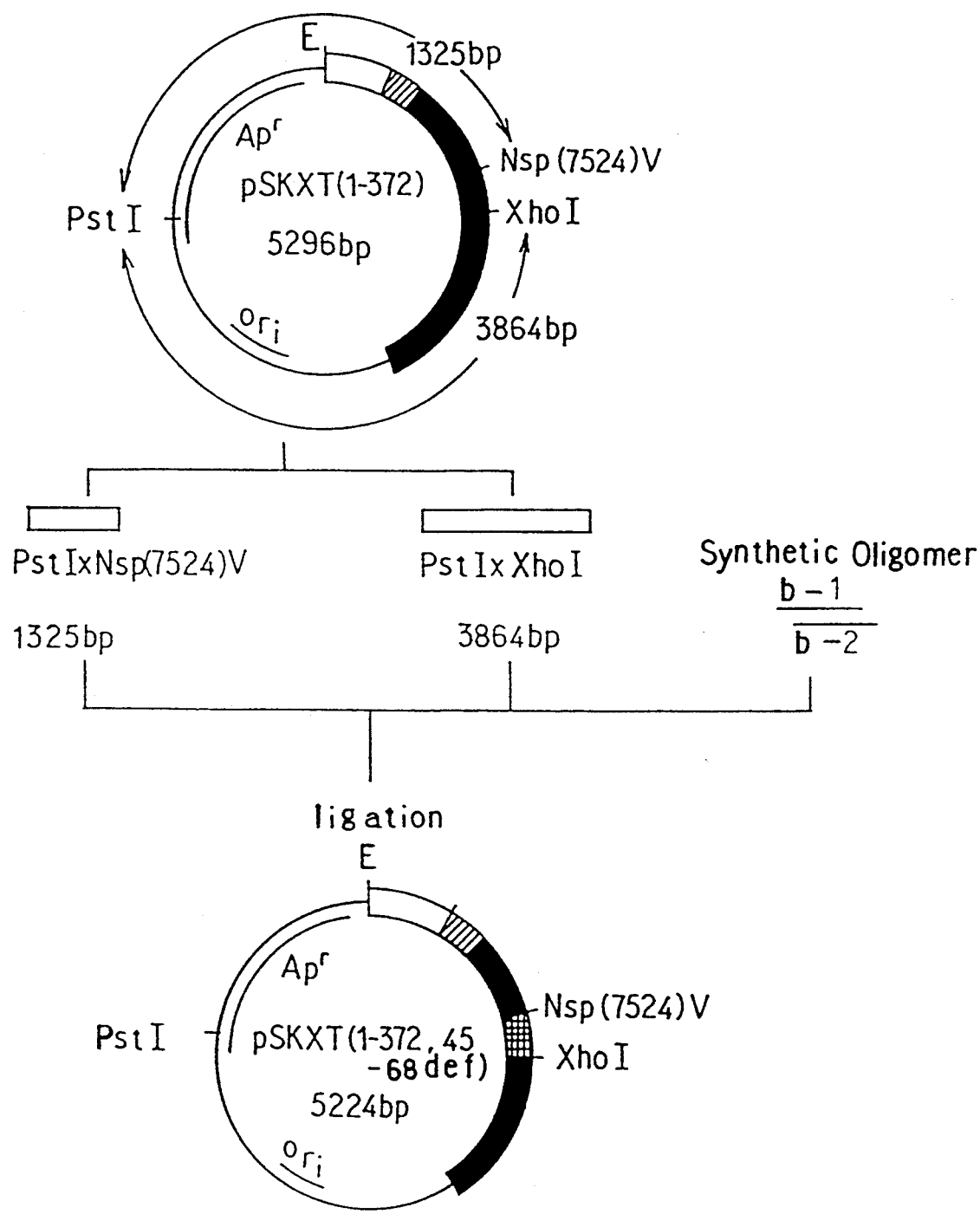
FIG. 6 is a diagram showing a procedure for preparing a vector for expressing streptokinase derivative protein (1-372, 45-68 deficient) in Example 7.

Preparation of Streptokinase Derivative Protein Expression Vector pSKXT (1-372, 45-68 Deficient) and Expression of the Protein A vector for expressing a streptokinase derivative protein (1-372, 45-68 deficient) was prepared by the following procedure using streptokinase derivative expression vector pSKXT (1-372) obtained in Example 5. FIG. 6 schematically shows the procedure. The desired vector is shown as "pSKXT (1-372, 45-68 def)" in the figure.

1) Chemical Synthesis of DNA Fragments

The desired derivative protein expression vector was prepared by replacing the sequence of pSKXT (1-372) at the region between restriction enzyme sites Nsp(7524)V and XhoI by the following freshly chemically synthesized oligonucleotide (DNA) fragments (b-1 and b-2).

```
(Nsp(7524) V)         b-1
CGAAATCGACCTGACCTCTGCTATGTCTCATAAAC
TTTAGCTGGACTGGAGACGATACAGAGTATTTGAGCT
         b-2                    (Xho I)
```

These fragments correspond to a region of streptokinase wherein the 45- to 68-positions are deficient and were individually chemically synthesized in the same manner as above.

2) Construction of pSKXT (1-372, 45-68 Deficient)

pSKXT (1-372) was treated with restriction enzymes PstI and Nsp(7524)V to form a DNA fragment of 1325 bp and with restriction enzymes PstI and XhoI to form a DNA fragment of 3864 bp. These fragments were collected by agarose gel electrophoresis and reacted with the two DNA fragments chemically synthesized by the procedure 1) above for ligation. *E. coli* JM109 was transformed with the reaction mixture, vector DNA was collected from the resulting colonies and purified, and a restriction enzyme map was prepared to obtain the desired vector pSKXT (1-372, 45-48 deficient).

3) Expression and Recognition of Derivative Protein (1-372, 45-68 Deficient)

*E. coli* JM109 harboring vector pSKXT (1-372, 45-68 deficient) obtained by the procedure 2) was incubated with shaking similarly using the same M-9 casamino acid liquid medium, and the cells were collected and checked for streptokinase activity (plasminogen activator activity). Consequently, an amount of expression of about 1200 international units/ml was detected from the cell fraction and was found almost entirely in the periplasm fraction. Further analysis by Western blotting revealed the immunoactivity at the position of calculated molecular weight of about 39600.

4) Preparation and Identification of Recombinant Streptokinase Derivative Protein (1-372, 45-68 Deficient)

In the same manner as in Example 5, 4), cells were collected from 800 ml of culture, and a periplasm fraction was extracted from the cells by the osmotic shock method. The desired derivative protein (1-372, 45-68 deficient) was collected from the extract, purified and lyophilized to obtain a purified product.

Table 9 below shows the result of amino acid analysis of the product.

TABLE 9

| Amino acid | Purified product | Calculated |
| --- | --- | --- |
| Asp | 54.3 | 57 |
| Thr | 24.9 | 25 |
| Ser | 19.2 | 20 |
| Glu | 36.7 | 36 |
| Pro | 13.9 | 14 |
| Gly | 13.9 | 14 |
| Ala | 17.0 | 17 |
| Val | 22.0 | 22 |
| ½ Cys | Not detected | 0 |
| Met | 3.8 | 4 |
| Ile | 20.0 | 22 |
| Leu | 36.6 | 36 |
| Tyr | 14.7 | 16 |
| Phe | 13.9 | 14 |
| Trp | Not detected | 1 |
| Lys | 27.2 | 27 |
| His | 6.8 | 7 |
| Arg | 15.1 | 16 |

The amount of recombinant streptokinase derivative protein (1-372, 45-68 deficient) obtained by the above method was found to be 2 mg by the amino acid analysis of a sample of the purified product.

The specific plasminogen activator activity was 112 in mole ratio based on that of the natural-type streptokinase which was taken as 100 and was comparable to that of the natural type.

EXAMPLE 8

Preparation of Streptokinase Derivative Protein Expression Vector pSKXT (1-372, 256Gln, 257Gln Replaced) and Expression of the Protein A vector for expressing a streptokinase derivative protein (1-372, replaced by Gln at each of the 256- and 257-positions) was prepared by the following procedure using streptokinase derivative expression vector pSKXT (1-372) obtained in Example 5.

Figure 7:
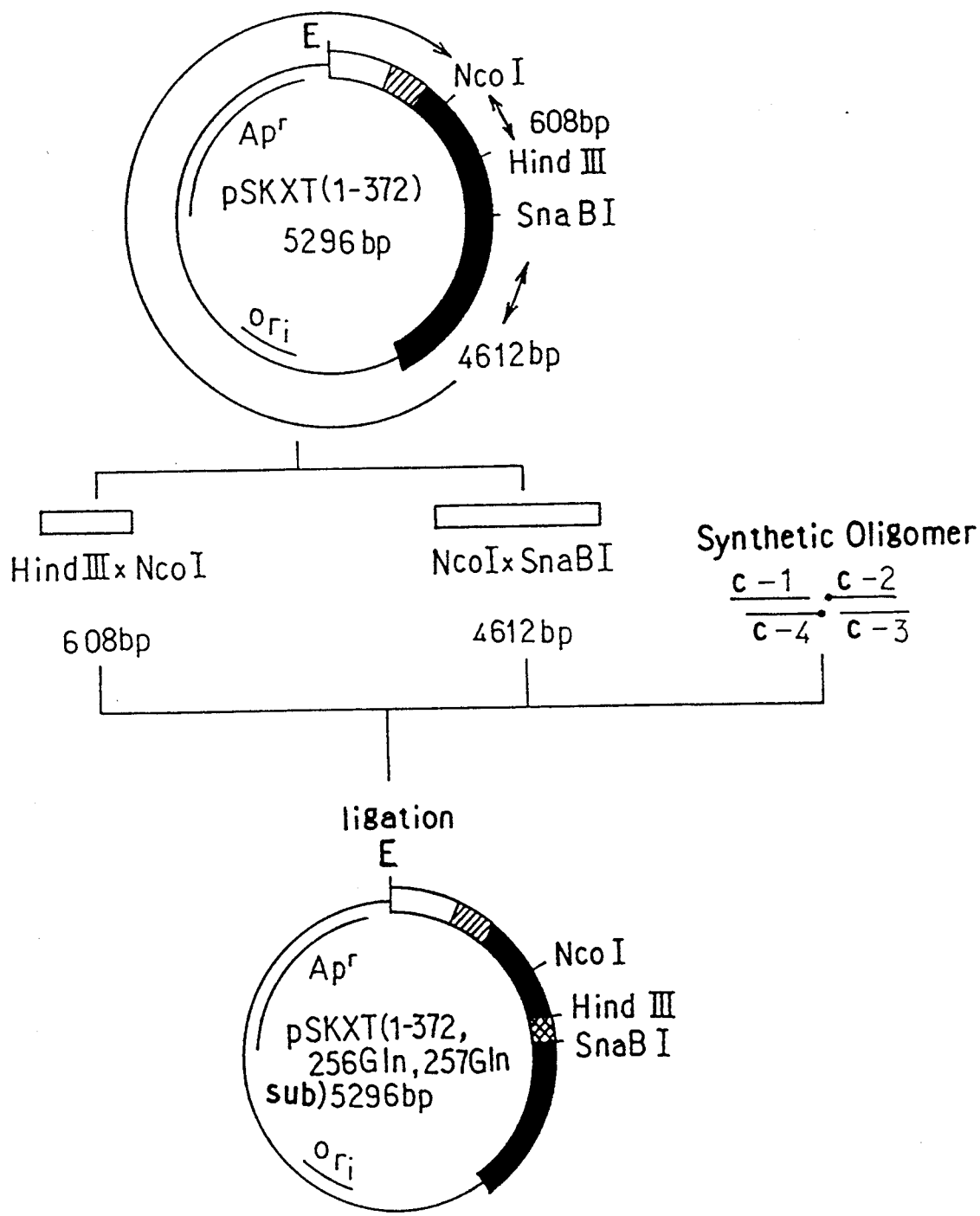
FIG. 7 is a diagram showing a procedure for preparing a vector for expressing streptokinase derivative protein (1-372, 256Gln, 257Gln replaced) in Example 8.

FIG. 7 schematically shows the procedure. The desired vector is shown as "pSKXT (1-372, 256Gln, 257Gln sub)" in the figure.

1) Chemical Synthesis of DNA Fragments

The desired derivative protein expression vector was prepared by replacing the sequence of pSKXT (1-372) at the region between restriction enzyme sites HindIII and SanBI by the following freshly chemically synthesized oligonucleotide (DNA) fragments (c-1 to c-4).

```
(Hind III)                  c-1
AGCTTACCGTATCAACCAGCAGTCTGGTCTGAATGAAG
    ATGGCATAGTTGGTCGTCAGACCAGACTTACTTC
                                    c-4 c-2
A GATTAACAACACTGACCTGATATCTGAAAAGTACTAC

TCTAAT TGTTGTGACTGGACTATAGACTTTTCATGATG
       c-3       (EcoR V)       (SnaB I)
```

These fragments include a region of streptokinase wherein Gln is substituted at each of the 256- and 257-positions. The four fragments c-1 to c-4 were individually chemically synthesized in the same manner as above. For the analysis to be practiced later, restriction enzyme recognition site EcoRV was further provided to the sequence.

2) Construction of pSKXT (1-372, 256Gln, 257Gln Replaced)

pSKXT (1-372) was treated with restriction enzymes HindIIII and NcoI to form a DNA fragment of 608 bp and with restriction enzymes NcoI and SnaBI to form a DNA fragment of 4612 bp. These fragments were collected by agarose gel electrophoresis and reacted with the four DNA fragments chemically synthesized by the procedure 1) above for ligation. (Oligomers c-2 and c-4 were used as phosphorylated at their 5' ends). *E. coli* JM109 was transformed with the reaction mixture, vector DNA was collected from the resulting colonies and purified, and a restriction enzyme map was prepared to obtain the desired vector.

3) Expression and Recognition of Derivative Protein (1-372, 256Gln, 257Gln Replaced)

*E. coli* JM109 harboring the vector obtained by the procedure 2) was incubated with shaking in the same manner as already stated using the same M-9 casamino acid liquid medium as above. After the addition of IPTG, the cells were collected and checked for streptokinase activity (plasminogen activator activity) similarly. As a result, no activity was detected from the medium supernatant but expression of about 70 international units/ml was detected from the cell fraction, i.e., almost entirely from the periplasm fraction. Further analysis by Western blotting revealed the immunoactivity at the position of calculated molecular weight of about 42300.

4) Preparation and Identification of Recombinant Streptokinase Derivative Protein (1-372, 256Gln, 257Gln Replaced)

In the same manner as in Example 5, 4), 2.4 liters of culture was centrifuged to collect the cells, from which a periplasm fraction was extracted by the osmotic shock method. The desired derivative protein (1-372, 256Gln, 257Gln replaced) was collected from the extract, purified and lyophilized to obtain a purified product.

When analyzed by SDS-PAGE in the presence of a reducing agent, the purified product exhibited a single band at the position of contemplated molecular weight of about 42300.

Table 10 below shows the result obtained by subjecting the purified product to amino acid analysis.

TABLE 10

| Amino acid | Purified product | Calculated |
| --- | --- | --- |
| Asp | 56.6 | 58 |
| Thr | 25.8 | 27 |
| Ser | 21.0 | 23 |
| Glu | 40.7 | 40 |
| Pro | 17.5 | 17 |
| Gly | 18.3 | 18 |
| Ala | 19.3 | 19 |
| Val | 19.9 | 22 |
| ½ Cys | Not detected | 0 |
| Met | 3.6 | 4 |
| Ile | 19.5 | 22 |
| Leu | 35.9 | 37 |
| Tyr | 15.5 | 16 |
| Phe | 15.1 | 15 |
| Trp | Not detected | 1 |
| Lys | 27.9 | 28 |
| His | 7.5 | 8 |
| Arg | 16.8 | 17 |

The amount of recombinant streptokinase derivative protein (1-372, 256Gln, 257Gln replaced) obtained by the above method was found to be 4 mg by the amino acid analysis of the purified product.

The specific plasminogen activator activity was in mole ratio based on that of the natural-type streptokinase which was taken as 100.

EXAMPLE 9

Preparation of Streptokinase Derivative Protein Expression Vector pSKXT (1-372, 118 Deficient, 256Gln, 257Gln Replaced) and Expression of the Protein A vector for expressing a streptokinase derivative protein (1-372, 118 deficient, 256Gln, 257Gln replaced) was prepared by the following procedure using streptokinase derivative expression vector pSKXT (1-372, 118 deficient) obtained in Example 6 and streptokinase derivative protein expression vector pSKXT (1-372, 256Gln, 257Gln replaced) obtained in Example 8.

Figure 8:
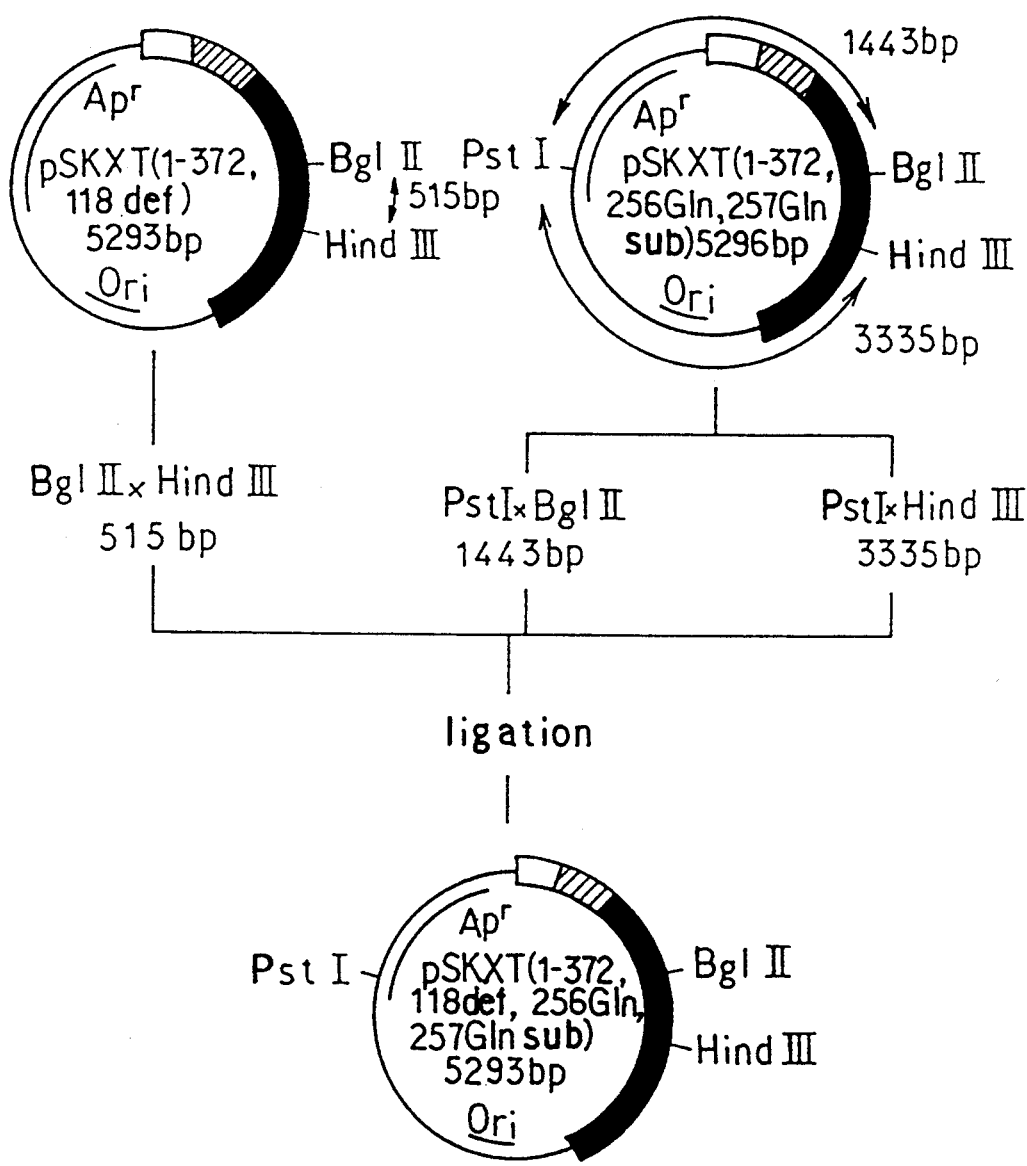
FIG. 8 is a diagram showing a procedure for preparing a vector for expressing streptokinase derivative protein (1-372, 118 deficient, 256Gln, 257Gln replaced) in Example 9.

FIG. 8 schematically shows the procedure. The desired vector is shown as "pSKXT (1-372, 118 def, 256Gln, 257Gln sub)" in the figure.

1) Construction of pSKXT (1-372, 118 Deficient, 256Gln, 257Gln Replaced)

pSKXT (1-372, 118 deficient) was treated with restriction enzymes BglII and HindIII to form a DNA fragment of 515 bp. pSKXT (1-372, 256Gln, 257Gln replaced) was treated with restriction enzymes PstI and BglII to form a DNA fragment of 1443 bp and with restriction enzymes PstI and HindIII to form a DNA fragment of 3335 bp. These DNA fragments were collected by agarose gel electrophoresis and ligated together by reaction. E. coli JM109 was transformed with the reaction mixture, vector DNA was collected from the resulting colonies and purified, and a restriction enzyme map was prepared to obtain the desired vector pSKXT (1-372, 118 deficient, 256Gln, 257Gln replaced).

2) Expression and Recognition of Derivative Protein (1-372, 118 Deficient, 256Gln, 257Gln Replaced)

E. coli JM109 harboring the vector obtained by the procedure 1) was incubated with shaking in the same manner as already stated using the same M-9 casamino acid liquid medium as above.

After the addition of IPTG, the cells were collected and checked for streptokinase activity (plasminogen activator activity) similarly. As a result, no activity was detected from the medium supernatant but expression of about 160 international units/ml was detected from the cell fraction, i.e., almost entirely from the periplasm fraction. Further analysis by Western blotting revealed the immunoactivity at the position of calculated molecular weight of about 42200.

3) Preparation and Identification of Recombinant Streptokinase Derivative Protein (1-372, 118 Deficient, 256Gln, 257Gln Replaced)

In the same manner as in Example 5, 4), 1.2 liters of culture was centrifuged to collect the cells, from which a periplasm fraction was extracted by the osmotic shock method. The desired derivative protein (1-372, 118 deficient, 256Gln, 257Gln replaced) was collected from the extract and purified.

When analyzed by SDS-PAGE in the presence of a reducing agent, the purified product exhibited a single band at the position of contemplated molecular weight of about 42200.

With addition of 6N hydrochloric acid, the purified product was hydrolyzed at 110° C. for 24 hours and subjected to amino acid analysis by the ninhydrin method using the automatic amino acid analyzer, Model Hitachi 835. Table 11 shows the result.

TABLE 11

| Amino acid | Purified product | Calculated |
| --- | --- | --- |
| Asp | 58.8 | 58 |
| Thr | 26.4 | 27 |
| Ser | 21.4 | 23 |
| Glu | 40.0 | 40 |
| Pro | 17.2 | 17 |
| Gly | 18.4 | 18 |
| Ala | 19.3 | 19 |
| Val | 19.9 | 22 |
| ½ Cys | Not detected | 0 |
| Met | 3.7 | 4 |
| Ile | 19.5 | 22 |
| Leu | 37.6 | 37 |
| Tyr | 15.7 | 16 |
| Phe | 13.9 | 14 |
| Trp | Not detected | 1 |
| Lys | 27.7 | 28 |
| His | 7.7 | 8 |
| Arg | 16.7 | 17 |

The amount of recombinant streptokinase derivative protein (1-372, 118 deficient, 256Gln, 257Gln replaced) obtained by the above method was found to be 5.4 mg by the amino acid analysis of the purified product.

The specific plasminogen activator activity was 9.98 in mole ratio based on that of the natural-type streptokinase which was taken as 100.

EXAMPLE 10

Preparation of Streptokinase Derivative Protein Expression Vector pSKXT (1-372, 45-68 Deficient, 256Gln, 257Gln Replaced) and Expression of the Protein A vector for expressing a streptokinase derivative protein (1-372, 45-68 deficient, 256Gln, 257Gln replaced) was prepared by the following procedure using streptokinase derivative expression vectors pSKXT (1-372, 45-68 deficient) and pSKXT (1-372, 256Gln, 257Gln replaced) obtained in Examples 7 and 8, respectively.

Figure 9:
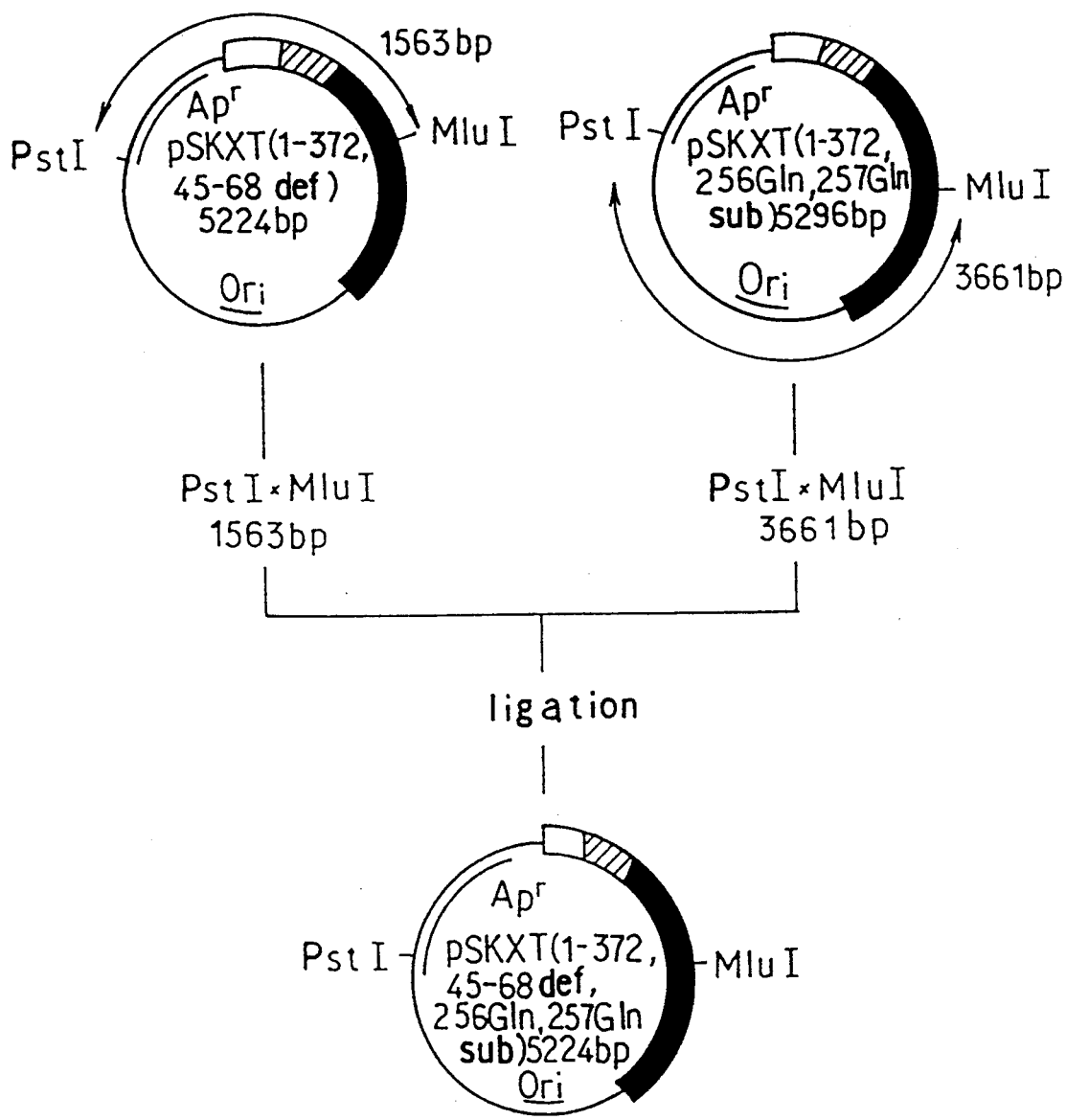
FIG. 9 is a diagram showing a procedure for preparing a vector for expressing streptokinase derivative protein (1-372, 45-68 deficient, 256Gln, 257Gln replaced) in Example 10.

FIG. 9 schematically shows the procedure. The desired vector is shown as "pSKXT (1-372, 45-68 def, 256Gln, 257Gln sub)" in the figure.

1) Construction of pSKXT (1-372, 45-68 Deficient, 256Gln, 257Gln Replaced)

pSKXT (1-372, 45-68 deficient) was treated with restriction enzymes PstI and MluI to form a DNA fragment of 1563 bp. pSKXT (1-372, 256Gln, 257Gln replaced) was treated with restriction enzymes PstI and MluI to form a DNA fragment of 3661 bp. These DNA fragments were collected by agarose gel electrophoresis and ligated together by reaction. E. coli JM109 was transformed with the reaction mixture, vector DNA was collected from the resulting colonies and purified, and a restriction enzyme map was prepared to obtain the desired vector pSKXT (1-372, 45-68 deficient, 256Gln, 257Gln replaced).

2) Expression and Recognition of Derivative Protein (1-372, 45-68 Deficient, 256Gln, 257Gln Replaced)

E. coli JM109 harboring the vector obtained by the procedure 1) was incubated with shaking in the same manner as already stated using the same M-9 casamino acid liquid medium as above.

After the addition of IPTG, the cells were collected and checked for streptokinase activity (plasminogen activator activity) similarly. As a result, no activity was detected from the medium supernatant but expression of about 40 international units/ml was detected from the cell fraction, i.e., almost entirely from the periplasm fraction. Further analysis by Western blotting revealed the immunoactivity at the position of calculated molecular weight of about 39800.

3) Preparation and Identification of Recombinant Streptokinase Derivative Protein (1-372, 45-68 Deficient, 256Gln, 257Gln Replaced)

In the same manner as in Example 5, 4), 0.8 liter of culture was centrifuged to collect the cells, from which a periplasm fraction was extracted by the osmotic shock method. The desired derivative protein (1-372, 45-68 deficient, 256Gln, 257Gln replaced) was collected from the extract and purified.

When analyzed by SDS-PAGE in the presence of a reducing agent, the purified product exhibited a single band at the position of contemplated molecular weight of about 39800.

With addition of 6N hydrochloric acid, the purified product was hydrolyzed at 110° C. for 24 hours and subjected to amino acid analysis by the ninhydrin method using the automatic amino acid analyzer, Model Hitachi 835. Table 12 shows the result.

TABLE 12

| Amino acid | Purified product | Calculated |
|---|---|---|
| Asp | 54.4 | 57 |
| Thr | 24.9 | 25 |
| Ser | 18.9 | 20 |
| Glu | 39.0 | 38 |
| Pro | 14.6 | 14 |
| Gly | 14.1 | 14 |
| Ala | 16.9 | 17 |
| Val | 21.5 | 22 |
| ½ Cys | Not detected | 0 |
| Met | 3.8 | 4 |
| Ile | 20.1 | 22 |
| Leu | 36.7 | 36 |
| Tyr | 15.2 | 16 |
| Phe | 13.9 | 14 |
| Trp | Not detected | 1 |
| Lys | 25.0 | 25 |
| His | 6.5 | 7 |
| Arg | 15.3 | 16 |

The amount of recombinant streptokinase derivative protein (1-372, 45-68 deficient, 256Gln, 257Gln replaced) obtained by the above method was found to be 0.56 mg by the amino acid analysis of the purified product.

The specific plasminogen activator activity was 6.30 in mole ratio based on that of the natural-type streptokinase which was taken as 100.

EXAMPLE 11

Preparation of Streptokinase Derivative Protein Expression Vector pSKXT (1-372, 45-68 Deficient, 118 Deficient, 256Gln, 257Gln Replaced) and Expression of the Protein A vector for expressing a streptokinase derivative protein (1-372, 45-68 deficient, 118 deficient, 256Gln, 257Gln replaced) was prepared by the following procedure using streptokinase derivative expression vectors pSKXT (1-372, 118 deficient) and pSKXT (1-372, 45-68 deficient, 256Gln, 257Gln replaced) obtained in Example 6 and 10, respectively.

Figure 10:
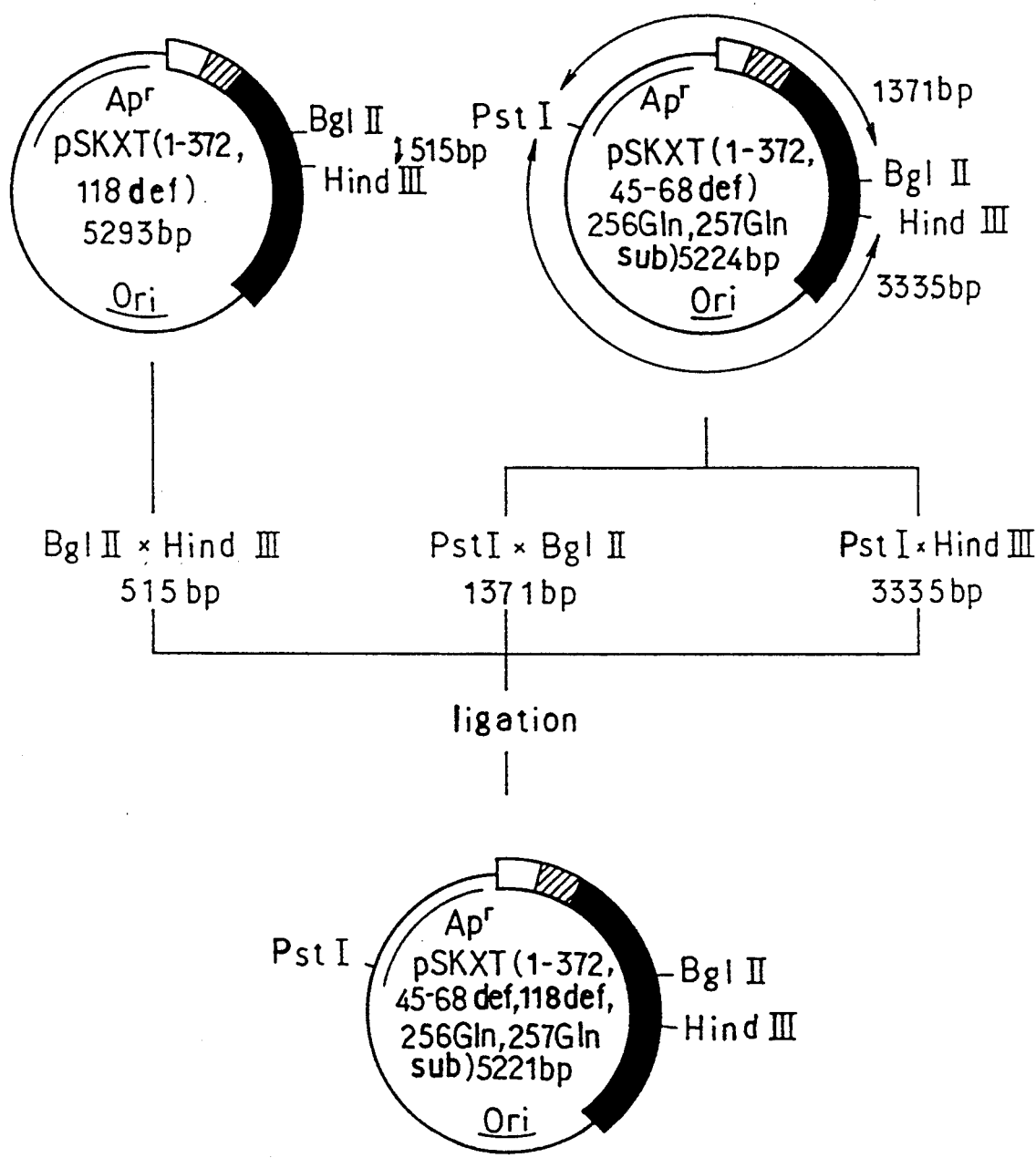
FIG. 10 is a diagram showing a procedure for preparing a vector for expressing streptokinase derivative protein (1-372, 45-68 deficient, 118 deficient, 256Gln, 257Gln replaced) in Example 11.

FIG. 10 schematically shows the procedure. The desired vector is shown as "pSKXT (1-372, 45-68 def, 118 def, 256Gln, 257Gln sub)" in the figure.

1) Construction of pSKXT (1-372, 45-68 Deficient, 118 Deficient, 256Gln, 257Gln Replaced)

pSKXT (1-372, 118 deficient) was treated with restriction enzymes BglII and HindIII to form a DNA fragment of 515 bp. pSKXT (1-372, 45-68 deficient, 256Gln, 257Gln replaced) was treated with restriction enzymes PstI and BglII to form a DNA fragment of 1371 bp and with restriction enzymes PstI and HindIII to form a DNA fragment of 3335 bp. These DNA fragments were collected by agarose gel electrophoresis and ligated by reaction. E. coli JM109 was transformed with the reaction mixture, vector DNA was collected from the resulting colonies and purified, and a restriction enzyme map was prepared to obtain the desired vector pSKXT (1-372, 45-68 deficient, 118 deficient, 256Gln, 257Gln replaced).

E. coli JM109 harboring the above vector has been deposited in Fermentation Research Institute, Agency of Industrial Science and Technology, MITI with the designation "Escherichia coli, JM-109, pSKXT (1-372, Δ45-68, Δ118, QQ")" and the deposition number FERM BP-2828.

2) Expression and Recognition of Derivative Protein (1-372, 45-68 Deficient, 118 Deficient, 256Gln, 257Gln Replaced)

E. coli JM109 (FERM BP-2828) harboring the vector obtained by the procedure 1) was incubated with shaking in the same manner as already stated using the same M-9 casamino acid liquid medium as above.

After the addition of IPTG, the cells were collected and checked for streptokinase activity (plasminogen activator activity) similarly. Consequently, no activity was detected from the medium supernatant but an amount of expression of about 170 international units/ml was detected from the cell fraction and was almost entirely found in the periplasm fraction. Further analysis by Western blotting revealed the immunoactivity at the position of calculated molecular weight of about 39700.

3) Preparation and Identification of Recombinant Streptokinase Derivative Protein (1-372, 45-68 Deficient, 118 Deficient, 256Gln, 257Gln Replaced)

In the same manner as in Example 5, 4), 1.2 liters of culture was centrifuged to collect the cells, from which a periplasm fraction was extracted by the osmotic shock method. The desired derivative protein (1-372, 45-68 deficient, 118 deficient, 256Gln, 257Gln replaced) was collected from the extract and purified.

When analyzed by SDS-PAGE in the presence of a reducing agent, the purified product exhibited a single band at the position of contemplated molecular weight of about 39700.

With addition of 6N hydrochloric acid, the purified product was hydrolyzed at 110° C. for 24 hours and subjected to amino acid analysis by the ninhydrin method using the automatic amino acid analyzer, Model Hitachi 835. Table 13 shows the result.

TABLE 13

| Amino acid | Purified product | Calculated |
|---|---|---|
| Asp | 57.8 | 57 |
| Thr | 24.6 | 25 |
| Ser | 18.7 | 20 |
| Glu | 37.9 | 38 |
| Pro | 14.4 | 14 |
| Gly | 14.1 | 14 |
| Ala | 17.0 | 17 |
| Val | 19.6 | 22 |
| ½ Cys | Not detected | 0 |
| Met | 3.6 | 4 |
| Ile | 19.5 | 22 |
| Leu | 36.2 | 36 |
| Tyr | 15.7 | 16 |
| Phe | 12.9 | 13 |
| Trp | Not detected | 1 |
| Lys | 24.5 | 25 |
| His | 7.1 | 7 |
| Arg | 16.1 | 16 |

The amount of recombinant streptokinase derivative protein (1-372, 45-68 deficient, 118 deficient, 256Gln, 257Gln replaced) obtained by the above method was found to be 2.4 mg by the amino acid analysis of the purified product.

The specific plasminogen activator activity was 7.74 in mole ratio based on that of the natural-type streptokinase which was taken as 100.

EXAMPLE 12

Preparation of Streptokinase Derivative Protein Expression Vector pSKXT (1-372, 256, 257Lys-Pro-Lys-Pro Altered) and Expression of the Protein A vector for expressing a streptokinase derivative protein (1-372, altered to -Lys-Pro-Lys-Pro- at the 256- and 257-positions) was prepared by the following procedure using streptokinase derivative expression vector pSKXT (1-372) obtained in Example 5.

Figure 11:
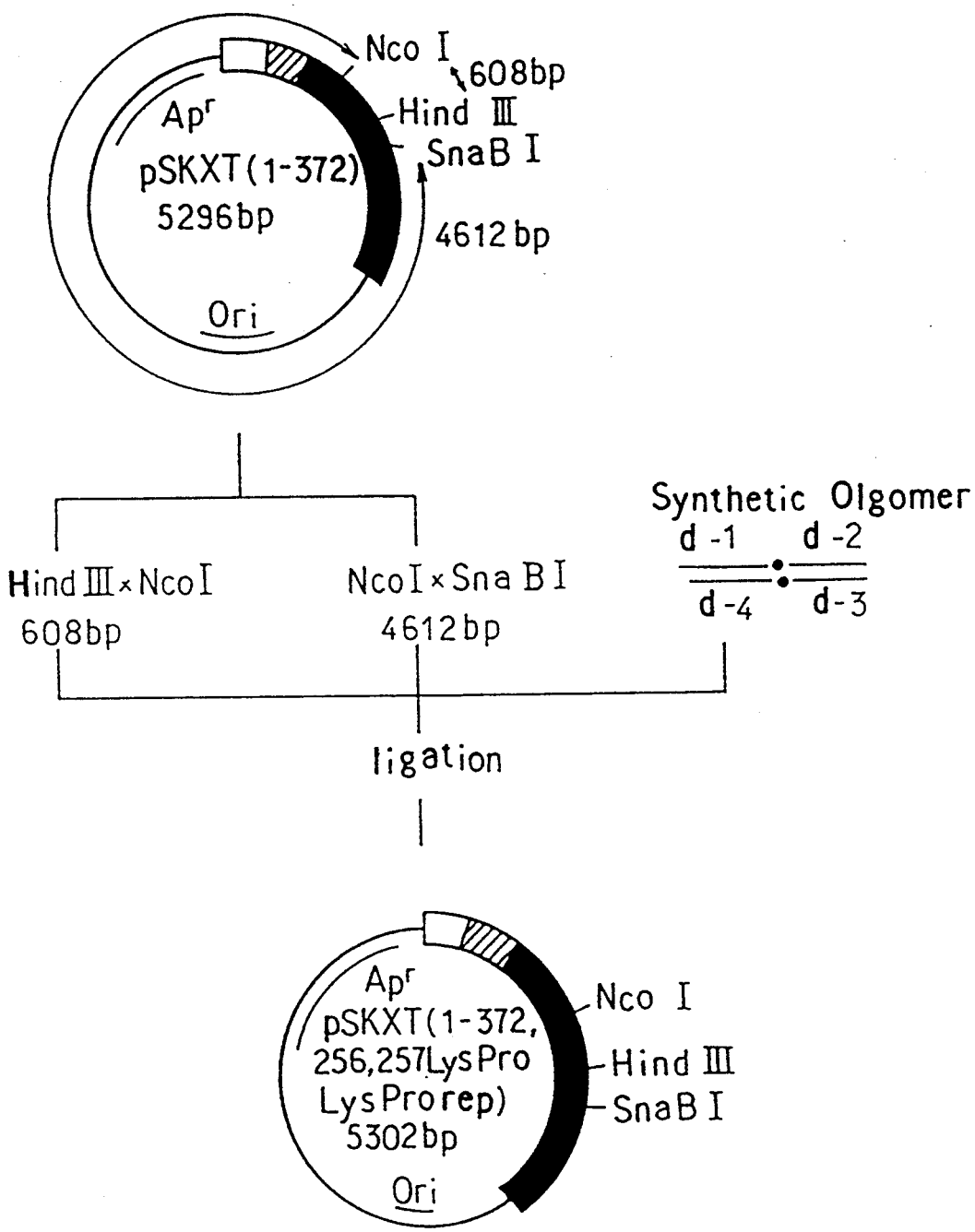
FIG. 11 is a diagram showing a procedure for preparing a vector for expressing streptokinase derivative protein (1-372, 256, 257Lys-Pro-Lys-Pro altered) in Example 12.

FIG. 11 schematically shows the procedure. The desired vector is shown as "pSKXT (1-372, 256, Lys-ProLysPro rep)" in the figure.

1) Chemical Synthesis of DNA Fragments

The desired derivative protein expression vector was prepared by replacing the sequence of pSKXT (1-372) at the region thereof between restriction enzyme recognition sites HindIII and SnaBI by the new DNA fragments d-1 to d-4 chemically synthesized and represented below.

```
(Hind III)           d-1
AGCTTACCGTATCAACAAACCGAAACCGTCTGGTCTGAATGAA
    ATGGCATAGTTGTTTGGCTTTGGCAGACCAGACTTACTT
                                         d-4
```

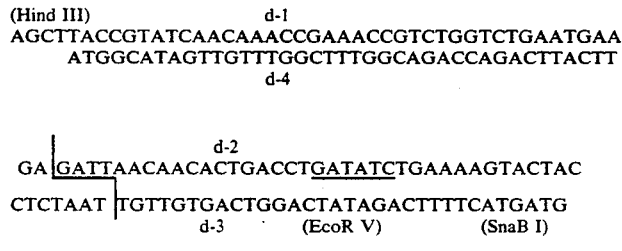

These fragments include Lys-Pro-Lys-Pro substituted for Lys-Lys at the 256- and 257-positions of streptokinase and are used for an alteration by replacing some amino acid residues by other amino acid residues according to the invention. The four oligonucleotides d-1 to d-4 were individually synthesized chemically. For the analysis to be performed later, new restriction enzyme recognition site EcoRV was provided.

2) Construction of pSKXT (1-372, 256, 257Lys-Pro-Lys-Pro Altered)

pSKXT (1-372) was treated with restriction enzymes HindIII and NcoI to form a DNA fragment of 608 bp and with restriction enzymes NcoI and SnaBI to form a DNA fragment of 4612 bp. These fragments were collected by agarose gel electrophoresis and reacted with the four chemically synthesized DNA fragments (with the oligomers d-2 and d-4 phosphorylated at the 5' ends). *E. coli* JM109 was transformed with the reaction mixture, vector DNA was collected from the resulting colonies and purified, and a restriction enzyme map was prepared to obtain the desired vector.

3) Expression and Recognition of Derivative Protein (1-372, 256, 257Lys-Pro-Lys-Pro altered)

*E. coli* JM109 harboring the vector obtained by the procedure 2) above was incubated with shaking in the same manner as already stated using the same M-9 casamino acid liquid medium as above.

After the addition of IPTG, the cells were collected and checked for streptokinase activity (plasminogen activator activity) similarly. Consequently, no activity was detected from the medium supernatant but an amount of expression of about 7 international units/ml was detected from the cell fraction and was almost entirely found in the periplasm fraction. Further analysis by Western blotting revealed the immunoactivity at the position of calculated molecular weight of about 42500.

4) Preparation and Identification of Recombinant Streptokinase Derivative Protein (1-372, 256, 257Lys-Pro-Lys-Pro Altered)

In the same manner as in Example 5, 4), 2.4 liters of culture was centrifuged to collect the cells, from which a periplasm fraction was extracted by the osmotic shock method. The desired derivative protein (1-372, 256, 257Lys-Pro-Lys-Pro altered) was collected from the extract and purified to obtain a lyophilized purified product.

When analyzed by SDS-PAGE in the presence of a reducing agent, the purified product exhibited a single band at the position of contemplated molecular weight of about 42500.

Table 14 below shows the result obtained by subjecting the purified product to amino acid analysis.

TABLE 14

| Amino acid | Purified product | Calculated |
|---|---|---|
| Asp | 60.6 | 58 |
| Thr | 27.2 | 27 |
| Ser | 22.4 | 23 |
| Glu | 38.7 | 38 |
| Pro | 18.1 | 19 |
| Gly | 18.5 | 18 |
| Ala | 19.9 | 19 |
| Val | 20.7 | 22 |
| ½ Cys | Not detected | 0 |
| Met | 3.4 | 4 |
| Ile | 20.2 | 22 |
| Leu | 38.3 | 37 |
| Tyr | 15.8 | 16 |
| Phe | 14.8 | 15 |
| Trp | Not detected | 1 |
| Lys | 30.1 | 30 |
| His | 8.1 | 8 |
| Arg | 16.1 | 17 |

The amount of recombinant streptokinase derivative protein (1-327, 356, 257Lys-Pro-Lys-Pro altered) thus obtained was found to be 0.46 mg by the amino acid analysis of the purified product.

The specific plasminogen activator activity was 17.7 in mole ratio based on that of the natural-type streptokinase which was taken as 100.

We claim:

1. A recombinant streptokinase derivative protein exhibiting streptokinase activity and consisting essentially of an amino acid sequence as shown in the following formula (1) or a variant thereof:

Ile—Ala—Gly—Pro—Glu—Trp—Leu—Leu—Asp—Arg—
Pro—Ser—Val—Asn—Asn—Ser—Gln—Leu—Val—Val—
Ser—Val—Ala—Gly—Thr—Val—Glu—Gly—Thr—Asn—
Gln—Asp—Ile—Ser—Leu—Lys—Phe—Phe—Glu—Ile—
Asp—Leu—Thr—Ser—Arg—Pro—Ala—His—Gly—Gly—
Lys—Thr—Glu—Gln—Gly—Leu—Ser—Pro—Lys—Ser—
Lys—Pro—Phe—Ala—Thr—Asp—Ser—Gly—Ala—Met—
Ser—His—Lys—Leu—Glu—Lys—Ala—Asp—Leu—Leu—
Lys—Ala—Ile—Gln—Glu—Gln—Leu—Ile—Ala—Asn—
Val—His—Ser—Asn—Asp—Asp—Tyr—Phe—Glu—Val—
Ile—Asp—Phe—Ala—Ser—Asp—Ala—Thr—Ile—Thr—
Asp—Arg—Asn—Gly—Lys—Val—Tyr—Phe—Ala—Asp—
Lys—Asp—Gly—Ser—Val—Thr—Leu—Pro—Thr—Gln—
Pro—Val—Gln—Glu—Phe—Leu—Leu—Ser—Gly—His—
Val—Arg—Val—Arg—Pro—Tyr—Lys—Glu—Lys—Pro—
Ile—Gln—Asn—Gln—Ala—Lys—Ser—Val—Asp—Val—

-continued
Glu—Tyr—Thr—Val—Gln—Phe—Thr—Pro—Leu—Asn—
Pro—Asp—Asp—Asp—Phe—Arg—Pro—Gly—Leu—Lys—
Asp—Thr—Lys—Leu—Leu—Lys—Thr—Leu—Ala—Ile—
Gly—Asp—Thr—Ile—Thr—Ser—Gln—Glu—Leu—Leu—
Ala—Gln—Ala—Gln—Ser—Ile—Leu—Asn—Lys—Asn—
His—Pro—Gly—Tyr—Thr—Ile—Tyr—Glu—Arg—Asp—
Ser—Ser—Ile—Val—Thr—His—Asp—Asn—Asp—Ile—
Phe—Arg—Thr—Ile—Leu—Pro—Met—Asp—Gln—Glu—
Phe—Thr—Tyr—Arg—Val—Lys—Asn—Arg—Glu—Gln—
Ala—Tyr—Arg—Ile—Asn—Lys—Lys—Ser—Gly—Leu—
Asn—Glu—Glu—Ile—Asn—Asn—Thr—Asp—Leu—Ile—
Ser—Glu—Lys—Tyr—Tyr—Val—Leu—Lys—Lys—Gly—
Glu—Lys—Pro—Tyr—Asp—Pro—Phe—Asp—Arg—Ser—
His—Leu—Lys—Leu—Phe—Thr—Ile—Lys—Tyr—Val—
Asp—Val—Asp—Thr—Asn—Glu—Leu—Leu—Lys—Ser—
Glu—Gln—Leu—Leu—Thr—Ala—Ser—Glu—Arg—Asn—
Leu—Asp—Phe—Arg—Asp—Leu—Tyr—Asp—Pro—Arg—
Asp—Lys—Ala—Lys—Leu—Leu—Tyr—Asn—Asn—Leu—
Asp—Ala—Phe—Gly—Ile—Met—Asp—Tyr—Thr—Leu—
Thr—Gly—Lys—Val—Glu—Asp—Asn—His—Asp—Asp—
Thr—Asn—Arg—Ile—Ile—Thr—Val—Tyr—Met—Gly—
Lys—Arg said variant consisting essentially of the amino acid sequence shown in formula (1) above and containing at least one of the following mutations:

(a) Phe at position 118 is deleted or replaced by another amino acid residue selected from the amino acids forming natural streptokinase;

(b) Lys position 256 is deleted or replaced by another amino acid residue selected from the amino acids forming natural streptokinase;

(c) Lys at position 257 is deleted or replaced by another amino acid residue selected from the amino acids forming natural streptokinase;

(d) an amino acid residue selected from the amino acids forming natural streptokinase is inserted between (i) Lys at position 256 and Lys at position 257, (ii) between Lys at position 257 and Ser at position 258 or (iii) between Lys at position 256 and Lys at position 257 and between Lys at position 257 and Ser at position 258; and (i) an amino acid sequence at any optional portion or the whole of between Arg at position 45 and Gly at position 68 is deleted.

2. The recombinant streptokinase derivative protein according to claim 1, wherein an amino acid sequence from Arg at position 45 to Gly at position 68 is deleted.

3. The recombinant streptokinase derivative protein according to claim 1, wherein Phe at position 118 is deleted or replaced by another amino acid residue selected from the amino acids forming natural streptokinase.

4. The recombinant streptokinase derivative protein according to claim 3, wherein said Phe at position 118 is deleted.

5. The recombinant streptokinase derivative protein according to claim 1, wherein Lys at position 256 and Lys at position 257 are both deleted or both replaced by another amino acid residue selected from the amino acids forming natural streptokinase.

6. The recombinant streptokinase derivative protein according to claim 5, wherein said another amino acid residue replacing Lys at position 256 is Gln, Thr or His.

7. The recombinant streptokinase derivative protein according to claim 5, wherein said another amino acid residue replacing Lys at position 257 is Pro, Gln, Ser or His.

8. The recombinant streptokinase derivative protein according to claim 1, wherein an amino acid residue selected from the amino acids forming natural streptokinase is inserted between (i) Lys at position 256 and Lys at position 257, (ii) between Lys at position 257 and Ser at position 258 or (iii) between Lys at position 256 and Lys at position 257 and between Lys at position 257 and Ser at position 258.

9. The recombinant streptokinase derivative protein according to claim 8, wherein said amino acid residue is Pro.

10. The recombinant streptokinase derivative protein according to claim 5, wherein Phe at position 118 is deleted or replaced by said another amino acid.

11. The recombinant streptokinase derivative protein according to claim 5, wherein Lys at position 256 and Lys at position 257 are each replaced by Gln.

12. The recombinant streptokinase derivative protein according to clam 11, wherein Phe at position 118 and the amino acid sequence from Arg at position 45 to Gly at position 68 are deleted.

13. The recombinant streptokinase derivative protein according to claim 1, wherein Lys at position 256 is deleted or replaced by another amino acid residue selected from the amino acids forming natural streptokinase.

14. The recombinant streptokinase derivative protein according to claim 1, wherein Lys at position 257 is deleted or replaced by another amino acid residue selected from the amino aids forming natural streptokinase.

* * * * *